United States Patent
Lee et al.

(10) Patent No.: US 9,617,261 B2
(45) Date of Patent: Apr. 11, 2017

(54) SUBSTITUTED PYRIDINONE COMPOUNDS AS MEK INHIBITORS

(71) Applicant: The Asan Foundation, Seoul (KR)

(72) Inventors: Gilnam Lee, Seoul (KR); Hye Sun Jeon, Gyeonggi-Do (KR); Ki Joon Jeon, Gyeonggi-Do (KR); Chul Yun Rhim, Seoul (KR); Jin Sung Kim, Seoul (KR); Jeongbeob Seo, Gyeonggi-Do (KR); Suk Young Cho, Chungcheongnam-Do (KR); Choung Soo Kim, Gyeonggi-Do (KR); Jung Shin Lee, Seoul (KR); Eun Kyung Choi, Seoul (KR); Jung Jin Hwang, Seoul (KR); Bongcheol Kim, Gyeonggi-Do (KR)

(73) Assignee: CMG PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 14/977,011

(22) Filed: Dec. 21, 2015

(65) Prior Publication Data

US 2016/0108041 A1    Apr. 21, 2016

Related U.S. Application Data

(63) Continuation of application No. PCT/KR2014/005464, filed on Jun. 20, 2014.

(60) Provisional application No. 61/837,402, filed on Jun. 20, 2013.

(51) Int. Cl.

| C07D 221/04 | (2006.01) |
|---|---|
| C07D 471/04 | (2006.01) |
| C07D 271/10 | (2006.01) |
| C07D 271/113 | (2006.01) |
| C07D 413/04 | (2006.01) |

(52) U.S. Cl.
CPC ......... *C07D 471/04* (2013.01); *C07D 221/04* (2013.01); *C07D 271/10* (2013.01); *C07D 271/113* (2013.01); *C07D 413/04* (2013.01)

(58) Field of Classification Search
CPC .................................................. C07D 221/04
USPC .............................................................. 546/112
See application file for complete search history.

(56) References Cited

U.S. PATENT DOCUMENTS

| 2009/0124595 A1 | 5/2009 | Adams et al. |
| 2012/0238599 A1 | 9/2012 | Lee et al. |

FOREIGN PATENT DOCUMENTS

| CN | 101626767 A | 1/2010 |
| WO | 2012/059041 A1 | 5/2012 |

OTHER PUBLICATIONS

Dubois et al., Tetrahedron (1996), 52(38), 12529-12540.*
International Search Report for International Application No. PCT/KR2014/005464, dated Dec. 3, 2014, 5 pages.
PubChem, SID 30591674 (Dec. 5, 2007) (http://pubchem.ncbi.nlm.nih.gov/summary/summary.cgi?sid=30591674) 3 pages.

* cited by examiner

*Primary Examiner* — Niloofar Rahmani
(74) *Attorney, Agent, or Firm* — Mintz Levin Cohn Ferris Glovsky and Popeo, P.C.; Kongsik Kim; Joohee Lee

(57) ABSTRACT

The invention provides novel substituted heterocyclic compounds represented by Formula I and Formula II, or a pharmaceutically acceptable salt, solvate, polymorph, ester, tautomer or prodrug thereof, and a composition comprising these compounds. The compounds provided can be used as inhibitors of MEK and are useful in the treatment of inflammatory diseases, cancer and other hyperproliferative diseases. The invention further provides a method of treatment for inflammatory diseases, cancer and other hyperproliferative diseases in mammals, especially humans.

7 Claims, 3 Drawing Sheets

SUBSTITUTED PYRIDINONE COMPOUNDS AS MEK INHIBITORS

CROSS-REFERENCE TO RELATED APPLICATIONS

This is a continuation application of International Application No. PCT/KR2014/005464 filed on Jun. 20, 2014, which claims priority to U.S. Application No. 61/837,402 filed on Jun. 20, 2013. The applications are incorporated herein by reference.

TECHNICAL FIELD

This invention relates to a series of substituted heterocyclic compounds which are inhibitors of MEK and are useful in the treatment of inflammatory diseases, cancer and other hyperproliferative diseases. This invention also relates to a pharmaceutical composition comprising the compound of the invention, use of the compound in the preparation of a medicament, and method of treatment for hyperproliferative diseases in mammals, especially humans by administering the compound thereof.

BACKGROUND ART

Protein kinases constitute a large family of structurally related enzymes that effect the transfer of a phosphate group from a nucleoside triphosphate to a Ser, Thr or Tyr residue on a protein acceptor. A vast array of cellular functions, including DNA replication, cell cycle progression, energy metabolism, and cell growth and differentiation, are regulated by reversible protein phosphorylation events mediated by protein kinases. Additionally, protein kinase activity has been implicated in a number of diseases, including cancers. Of the >100 dominant oncogenes known to date, many encode receptor and cytoplasmic protein kinases known to be mutated and/or over expressed in human cancers (Blume-Jensen and Hunter, Nature, 411:355-365 (2001)). Accordingly, protein kinase targets have attracted substantial drug discovery efforts in recent years, with several protein kinase inhibitors achieving regulatory approval (reviewed in Fischer, Curr. Med. Chem., 11:1563 (2004); Dancey and Sausville, Nature Rev. Drug Disc., 2:296 (2003)).

The Ras/Raf/MEK/ERK pathway is a central signal transduction pathway, which transmits signals from multiple cell surface receptors to transcription factors in the nucleus which regulate gene expression. This pathway is frequently referred to as the MAP kinase pathway as MAPK stands for mitogen-activated protein kinase indicating that this pathway can be stimulated by mitogens, cytokines and growth factors (Steelman et al., Leukemia 2004, 18, 189-218). Depending upon the stimulus and cell type, this pathway can transmit signals, which result in the prevention or induction of apoptosis or cell cycle progression. The Ras/Raf/MEK/ERK pathway has been shown to play important roles in cell proliferation and the prevention of apoptosis. Aberrant activation of this pathway is commonly observed in malignantly transformed cells. Amplification of ras proto-oncogenes and activating mutations that lead to the expression of constitutively active Ras proteins are observed in approximately 30% of all human cancers (Stirewalt et al., Blood 2001, 97, 3589-95). Mutated, oncogenic forms of Ras are found in 50% of colon and >90% pancreatic cancers as well as many other types of cancers (Kohl et al., Science 1993, 260, 1834-1837). The effects of Ras on proliferation and tumorigenesis have been documented in immortal cell lines (Mc-Cubrey et al., Int J Oncol 1995, 7, 295-310). bRaf mutations have been identified in more than 60% of malignant melanoma (Davies, H et al., Nature 2002, 417, 949-954). Given the high level of mutations that have been detected at Ras, this pathway has always been considered a key target for therapeutic intervention (Chang et al., Leukemia 2003, 17, 1263-93).

As constitutive or overactivation of MAP kinase cascade plays a pivotal role in cell proliferation and differentiation, inhibition of this pathway is believed is to be beneficial in hyperproliferative diseases. MEK is a key player in this pathway as it is downstream of Ras and Raf. Additionally, it is an attractive therapeutic target because the only known substrates of MEK phosphorylation are the MAP kinases, ERK1 and ERK2. Inhibition of MEK has been shown to have potential therapeutic benefit in several studies. For example, small molecule MEK inhibitors have been shown to inhibit human tumor growth in mouse xenografts, (See-bolt-Leopold et. al., Nature-Medicine, 1999 5(7), 810-816; Trachet et al. AACR Apr. 6-10, 2002, Poster & num; 5426) and inhibit growth of acute myeloid leukemia cells (Milella et. al., J. Clin. Invest., 2001, 108 (6) 851-859).

Compounds suitable as MEK inhibitors are also disclosed in WO 00/41994; WO 00/42022; WO 00/42029; WO 00/68201; WO 01/68619; WO 02/06213, WO 03/077914, WO 05/023251, WO 05/121142, WO07/014011, WO 07/071951, WO 07/123939, WO 08/021389, WO 08/078086, WO 08/120004, WO 08/124085, WO 08/125180, WO 09/018233, WO07/044084, WO07/121481, WO 09/018238 and WO10108852.

SUMMARY

The invention is to provide novel substituted heterocyclic compounds represented by Formula I and Formula II, or a pharmaceutically acceptable salt, solvate, polymorph, ester, tautomer or prodrug thereof, and a composition comprising these compounds, wherein the compounds can be used as inhibitors of MEK and are useful in the treatment of inflammatory diseases, cancer and other hyperproliferative diseases.

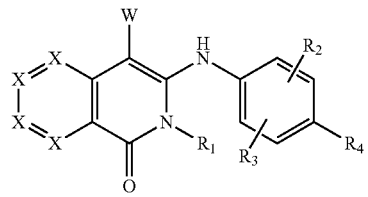

Formula I

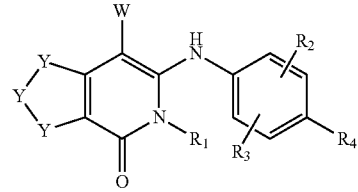

Formula II

Furthermore, the invention is to provide a method of treatment for inflammatory diseases, cancer and other hyperproliferative diseases in mammals, especially humans.

This invention provides a compound of formula I or formula II, or a pharmaceutically acceptable salt, solvate, polymorph, ester, tautomer or prodrug thereof:

Formula I

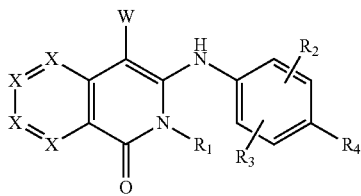

Formula II

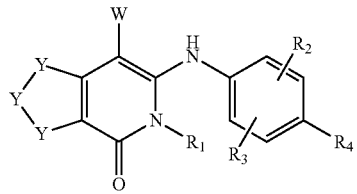

wherein $R_1$ is H, $C_1$-$C_6$ alkyl, $C_3$-$C_6$ cycloalkyl, $C_2$-$C_6$ alkenyl, $C_5$-$C_6$ cycloalkenyl or $C_2$-$C_6$ alkynyl; wherein each alkyl, cycloalkyl, alkenyl, cycloalkenyl or alkynyl group is optionally substituted with 1-3 substituents selected independently from the group consisting of halogen, hydroxy, $C_1$-$C_4$ alkyl, $C_1$-$C_4$ alkoxy, cyano, cyanomethyl, trifluoromethyl, difluoromethoxy and phenyl, and one or two ring carbon atoms of said $C_3$-$C_6$ cycloalkyl groups are optionally replaced with, independently, O, N, or S; and $R_2$, $R_3$, and $R_4$ are independently selected from hydrogen, halogen, cyano, nitro, trifluoromethyl, difluoromethyl, fluoromethyl, fluoromethoxy, difluoromethoxy, trifluoromethoxy, azido, —$SR_9$, —$OR_9$, —$C(O)R_9$, —$NR_{10}C(O)OR_{12}$, —$OC(O)R_9$, —$NR_{10}$, —$S(O)_jR_{12}$, —$S(O)_jNR_9R_{10}$, —$S(O)_jNR_{10}C(O)R_9$, —$C(O)NR_{10}S(O)_jR_{12}$, —$S(O)_jR_{12}$, —$NR_{10}C(O)R_9$, —$C(O)NR_9R_{10}$, —$NR_{11}C(O)NR_9R_{10}$, —$NR_{11}C(NCN)NR_9R_{10}$, —$NR_9R_{10}$ and $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR_{10}R_{11})_m$-aryl, aryl, arylalkyl, heteroaryl, heteroarylalkyl, heterocyclyl, heterocyclylalkyl, —$O(CR_{10}R_{10})_m$-aryl, —$NR_{10}(CR_{10}R_{11})_m$-aryl, —$O(CR_{10}R_{11})_m$-heteroaryl, —$NR_{10}(CR_{10}R_{11})_m$-heteroaryl, —$O(CR_{10}R_{11})_m$-heterocyclyl, —$NR_{10}(CR_{10}R_{11})_m$-heterocyclyl, and —$S(C_1$-$C_2$ alkyl) optionally substituted with fluorine atoms;

$R_9$ is selected from the group consisting of hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is unsubstituted or substituted with 1-3 substituents independently selected from the group consisting of halogen, $C_1$-$C_4$ alkyl, hydroxyl and amino;

$R_{10}$ is selected from hydrogen or $C_1$-$C_6$ alkyl where alkyl may be unsubstituted or substituted with 1-3 substituents independently selected from the group consisting of halogen, $C_1$-$C_4$ alkyl, hydroxyl and amino; or $R_9$ and $R_{10}$ can be taken together with the atom to which they are attached to form a 4 to 10 membered heteroaryl or heterocyclic ring, each of which is unsubstituted or substituted with 1-3 substituents independently selected from the group consisting of halogen, $C_1$-$C_4$ alkyl, hydroxyl and amino;

$R_{11}$ is selected from hydrogen or $C_1$-$C_6$ alkyl where alkyl may be unsubstituted or substituted with 1-3 substituents independently selected from the group consisting of halogen, $C_1$-$C_4$ alkyl, hydroxyl and amino; or $R_{10}$ and $R_{11}$ can be taken together with the atom to which they are attached to form a 4 to 10 membered carbocyclic, heteroaryl or heterocyclic ring, each of which is unsubstituted or substituted with 1-3 substituents independently selected from the group consisting of halogen, $C_1$-$C_4$ alkyl, hydroxyl and amino, and $R_{12}$ is selected from trifluoromethyl, $C_1$-$C_{10}$ alkyl, $C_3$-$C_{10}$ cycloalkyl, aryl, arylalkyl, heteroaryl, heteroarylalkyl, heterocyclyl, and heterocyclylalkyl, where each alkyl, cycloalkyl, aryl, heteroaryl and heterocyclyl unsubstituted or substituted with 1-3 substituents independently selected from the group consisting of halogen, $C_1$-$C_4$ alkyl, hydroxyl and amino;

W is —$C(O)OR_6$, —$C(O)NR_6R_7$, —$C(O)NR_7OR_6$, —$C(O)R_7OR_6$, heteroaryl, heterocyclyl, —$NHSO_2R_6$, —$NHC(O)OR_6$, —$NHC(O)NR_6R_7$, —$NHC(O)R_6$, —$NR_6R_7$, —$C(O)(C_3$-$C_{10}$ cycloalkyl), —$C(O)(C_1$-$C_{10}$ alkyl), —$C(O)(aryl)$, —$C(O)(heteroaryl)$, —$C(O)(heterocyclyl)$, —$C(O)NHSO_2CH_3$, or —$CR_6OR_6$, wherein any of said heteroaryl, heterocyclyl, —$C(O)OR_6$, —$C(O)NR_6R_7$, —$C(O)NR_7OR_6$, —$C(O)R_7OR_6$, —$NHSO_2R_6$, —$NHC(O)OR_6$, —$NHC(O)NR_6R_7$, —$NHC(O)R_6$, —$NR_6R_7$, —$C(O)(C_3$-$C_{10}$ cycloalkyl), —$C(O)(C_1$-$C_{10}$ alkyl), —$C(O)(aryl)$, —$C(O)(heteroaryl)$, —$C(O)(heterocyclyl)$, —$C(O)NHSO_2CH_3$ and —$CR_6OR_6$ are optionally substituted independently with one or more groups independently selected from halogen, cyano, nitro, azide, —$NR_6R_7$, —$OR_6$, $C_1$-$C_{10}$ alkyl, $C_2$-$C_{10}$ alkenyl, and $C_2$-$C_{10}$ alkynyl, cycloalkyl and heterocycloalkyl, wherein any of said $C_1$-$C_{10}$ alkyl, $C_2$-$C_{10}$ alkenyl, $C_2$-$C_{10}$ alkynyl, cycloalkyl and heterocycloalkyl are optionally substituted independently with 1 or more groups independently selected from —$NR_6R_7$ and —$OR_6$;

$R_6$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that is not substituted on a aryl or heteroaryl), halogen, cyano, nitro, trifluoromethyl, difluoromethoxy, trifluoromethoxy, azido, —$NR_{13}SO_2R_{16}$, —$SO_2NR_{13}R_{14}$, —$C(O)R_{13}$, —$C(O)OR_{13}$, —$OC(O)R_{13}$, —$NR_{13}C(O)OR_{16}$, —$NR_{13}C(O)R_{14}$, —$C(O)NR_{13}R_{14}$, —$SR_{13}$, —$S(O)R_{16}$, —$SO_2R_{16}$, —$NR_{13}R_{14}$, —$NR_{13}C(O)NR_{14}R_{15}$, —$NR_{13}C(NCN)NR_{14}R_{15}$, —$OR_{13}$, aryl, heteroaryl, arylalkyl, heteroarylalkyl, heterocyclyl, and heterocyclylalkyl, or $R_6$ and $R_7$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —$NR_{13}SO_2R_{16}$, —$SO_2NR_{13}R_{14}$, —$C(O)R_{13}$, —$C(O)OR_{13}$, —$OC(O)R_{13}$, —$NR_{13}C(O)OR_{16}$, —$NR_{13}C(O)R_{14}$, —$C(O)NR_{13}R_{14}$, —$SO_2R_{16}$, —$NR_{13}R_{14}$, —$NR_{13}C(O)NR_{14}R_{15}$, —$NR_{13}C(NCN)NR_{14}R_{15}$, —$OR_{13}$, aryl, heteroaryl, arylalkyl, heteroarylalkyl, heterocyclyl, and heterocyclylalkyl;

$R_7$ is hydrogen or $C_1$-$C_6$ alkyl;

each X is independently N or $CR_5$;

each Y is independently $CH_2$, $C(CH_3)_2$ or $CR_{17}R_{17}$;

m is 0, 1, 2, 3, 4 or 5; and j is 1 or 2.

R$_5$ is H, F, Cl, Br, CF$_3$, CN, —C(O)R$_6$, —C(O)OR$_6$, —C(O)NR$_6$R$_7$, —NR$_6$R$_7$, —NR$_6$C(O)R$_7$, —NR$_8$C(O)OR$_7$, —NR$_8$C(O)NR$_6$R$_7$, —NR$_B$, —SO$_2$NR$_6$R$_7$, —OR$_6$, —OC(O)R$_6$, —OC(O)OR$_6$, —OC(O)NR$_6$R$_7$, —SR$_6$, —SO$_2$R$_6$, —SO$_2$NR$_6$R$_7$, C$_1$-C$_{12}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, or heterocyclylalkyl;

R$_8$ is selected from the group consisting of trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heteroarycycloalkyl, heterocyclyl, and heterocyclylalkyl, where each alkyl, alkenyl, alkynyl, cycloalkyl, cycloalkylalkyl, aryl, arylalkyl, heteroaryl, heteroarylalkyl, heterocyclylalkyl, heteroarycycloalkyl, and heterocyclyl is unsubstituted or substituted with 1-3 substituents selected independently from halogen, hydroxyl, C$_1$-C$_4$ alkyl, C$_1$-C$_4$ alkoxy, cyano, trifluoromethyl, difluoromethoxy, phenyl or substituted phenyl with 1-3 substituents selected independently from halogen, hydroxyl, C$_1$-C$_4$ alkyl, C$_1$-C$_4$ alkoxy, cyano trifluoromethyl, or difluoromethoxy;

R$_{13}$, R$_{14}$ and R$_{15}$ independently are hydrogen, lower alkyl, lower alkenyl, aryl and arylalkyl, and R$_{16}$ is lower alkyl, lower alkenyl, aryl and arylalkyl, or any two of R$_{13}$, R$_{14}$, R$_{15}$ or R$_{16}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

each R$_{17}$ is independently selected from the group consisting of hydrogen, halo, nitro, cyano, thio, oxy, hydroxy, carbonyloxy, C$_1$-C$_{10}$ alkoxy, C$_4$-C$_{12}$ aryloxy, heteroC$_1$-C$_{10}$ aryloxy, carbonyl, oxycarbonyl, aminocarbonyl, amino, C$_1$-C$_{10}$ alkylamino, sulfonamido, imino, sulfonyl, sulfinyl, C$_1$-C$_{10}$ alkyl, haloC$_1$-C$_{10}$ alkyl, hydroxylC$_1$-C$_{10}$ alkyl, carbonylC$_1$-C$_{10}$ alkyl, thiocarbonylC$_1$-C$_{10}$ alkyl, sulfonylC$_1$-C$_{10}$ alkyl, sulfinylC$_1$-C$_{10}$ alkyl, C$_1$-C$_{10}$ alzalkyl, iminoC$_1$-C$_{10}$ alkyl, C$_3$-C$_{12}$ cycloalkylC$_1$-C$_5$ alkyl, heteroC$_3$-C$_{12}$ cycloalkylC$_1$-C$_{10}$ alkyl, arylC$_1$-C$_{10}$ alkyl, heteroC$_1$-C$_{10}$ arylC$_1$-C$_5$ alkyl, C$_9$-C$_{12}$ bicycloarylC$_1$-C$_5$ alkyl, heteroC$_8$-C$_{12}$ bicycloarylC$_1$-C$_5$ alkyl, C$_3$-C$_{12}$ cycloalkyl, heteroC$_3$-C$_{12}$ cycloalkyl, C$_9$-C$_{12}$ bicycloalkyl, heteroC$_3$-C$_{12}$ bicycloalkyl, C$_4$-C$_{12}$ aryl, heteroC$_1$-C$_{10}$ aryl, C$_9$-C$_{12}$ bicycloaryl and heteroC$_4$-C$_{12}$ bicycloaryl, each substituted or unsubstituted, or two R$_{17}$ are taken together to form a substituted or unsubstituted ring.

In another aspect, the present invention provides some preferable compounds of Formula I or Formula II, wherein R$_1$ is H or C$_1$-C$_6$ alkyl; or a pharmaceutically acceptable salt, solvate, polymorph, ester, tautomer or prodrug thereof.

In another aspect, the present invention provides some preferable compounds of Formula I or Formula II, wherein R$_2$, R$_3$ and R$_4$ are independently selected from H or halogen; or a pharmaceutically acceptable salt, solvate, polymorph, ester, tautomer or prodrug thereof.

In another aspect, the present invention provides some preferable compounds of Formula I or Formula II, wherein one of R$_2$ and R$_3$ is fluoro or chloro, and R$_4$ is iodo; or a pharmaceutically acceptable salt, solvate, polymorph, ester, tautomer or prodrug thereof.

Exemplary embodiments of Formula I and II compounds include, but are not limited to, the following structures;

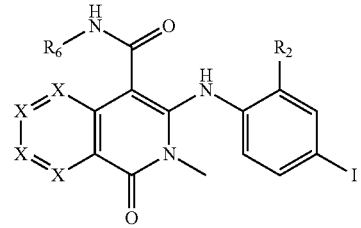

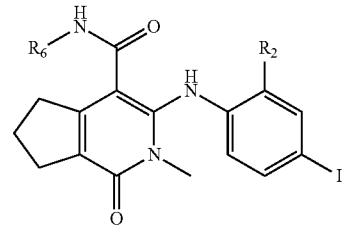

In certain embodiments, each X is independently CH or N.

In certain embodiments, R$_2$ is F or Cl.

Exemplary embodiments of R$_6$ include, but are not limited to, the following structures:

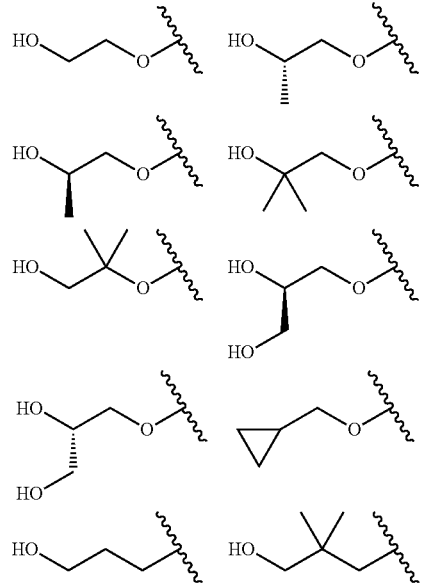

Exemplary embodiments of Formula I and II compounds include, but are not limited to, the following structures;

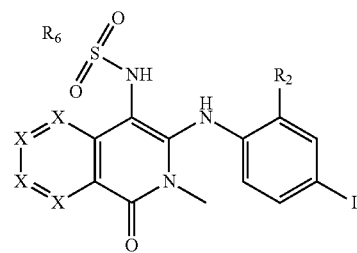

-continued

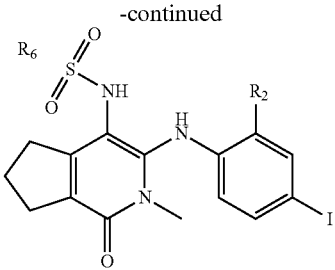

In certain embodiments, each X is independently CH or N.

In certain embodiments, $R_2$ is F or Cl.

Exemplary embodiments of $R_6$ include, but are not limited to, the following structures:

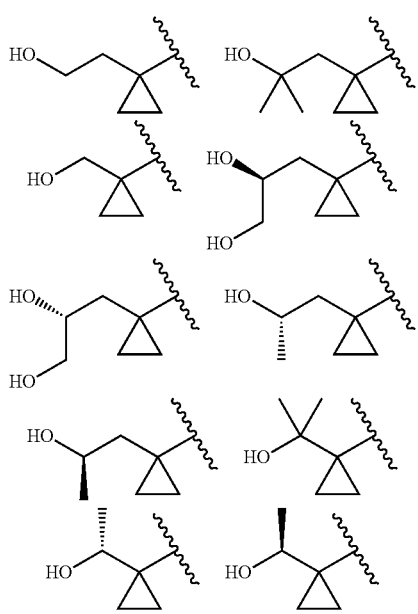

Exemplary embodiments of Formula I and II compounds include, but are not limited to, the following structures:

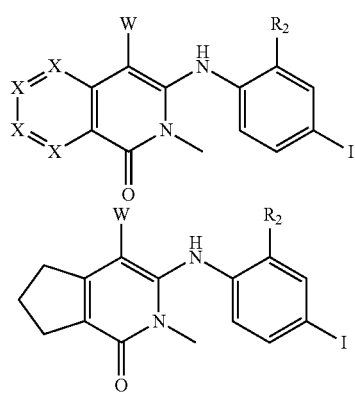

In certain embodiments, each X is independently CH or N.

In certain embodiments, $R_2$ is F or Cl.

In certain embodiments, W is optionally substituted heteroaryl, or heterocyclyl.

Exemplary embodiments of W include, but are not limited to, the following structures:

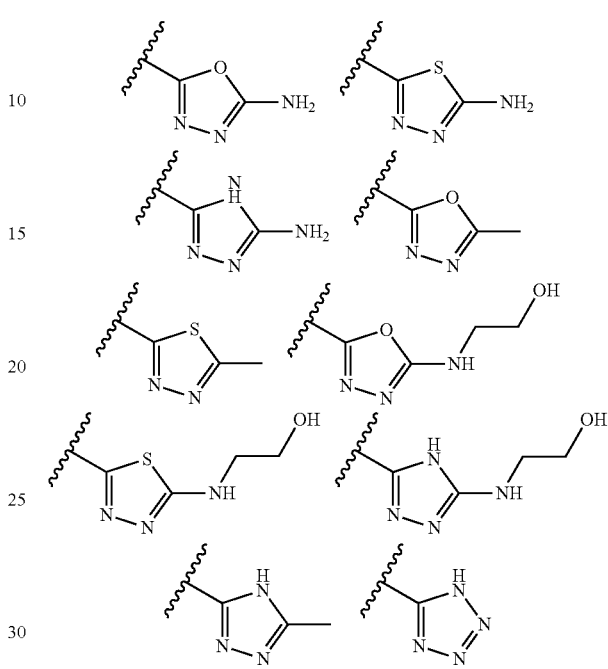

In certain embodiments, the present invention provides compounds represented by the following Formula:

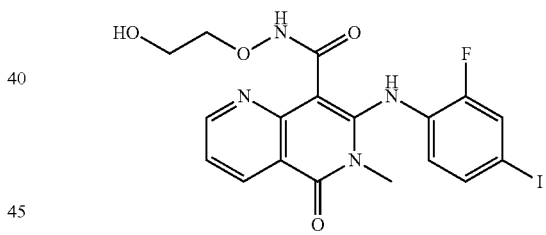

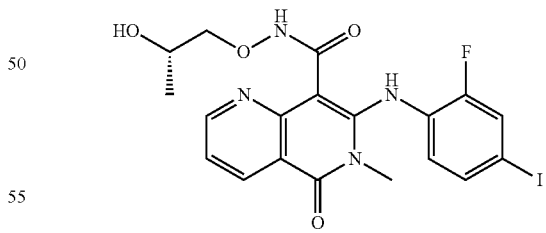

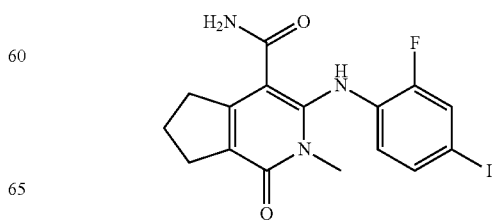

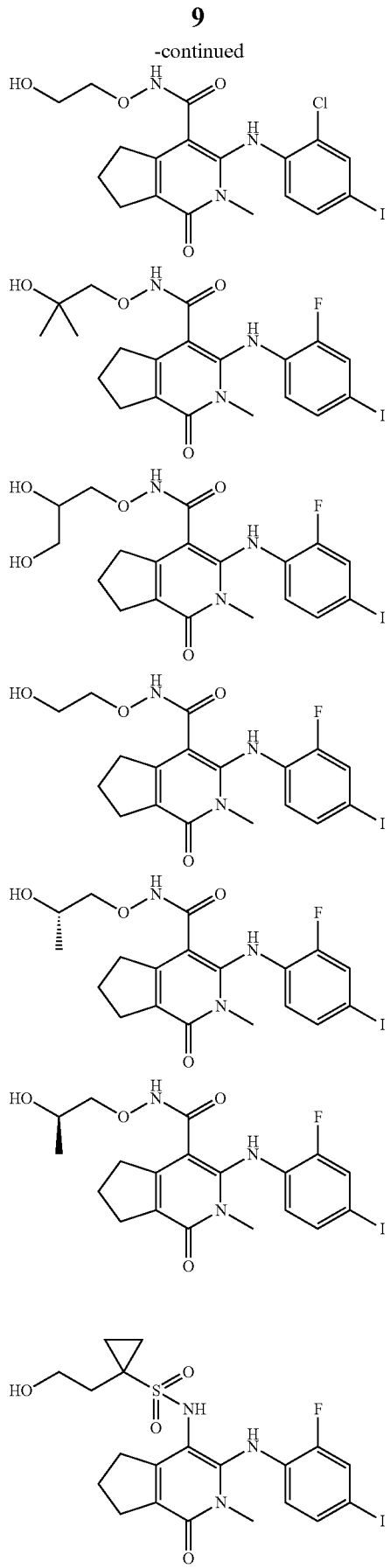

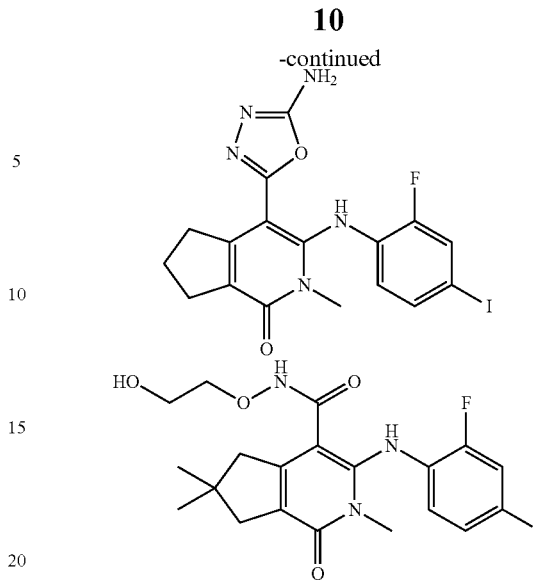

or a pharmaceutically acceptable salt, solvate, polymorph, ester, tautomer or prodrug thereof.

Compounds of present invention are inhibitors of MEK and, consequently, are useful for treating cancers and other hyperproliferative diseases.

In other aspects, the present invention is directed to a pharmaceutical composition comprising an effective amount of a compound of formula I or formula II or a pharmaceutically acceptable salt, solvate, polymorph, ester, tautomer or prodrug thereof. In some embodiments, the pharmaceutical composition further comprises a pharmaceutically acceptable carrier, adjuvants and/or excipients. In some embodiments, such a composition may contain at least one of preservatives, agents for delaying absorption, fillers, binders, adsorbents, buffers, disintegrating agents, solubilizing agents, and other carriers, adjuvants and/or excipients as inert ingredients. The composition may be formulated with a method well-known in the art.

In some aspects, the present invention is directed to a method of treating a disease in an individual suffering from said disease comprising administering to said individual a therapeutically effective amount of a composition comprising a compound of formula I or formula II or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of a compound of formula I or formula II or a pharmaceutically acceptable salt, solvate, polymorph, ester, tautomer or pro-drug thereof.

In other aspects, the present invention is directed to a method of treating a disorder in a human, comprising administering to said human a therapeutically effective amount of a compound of formula I or formula II or a pharmaceutically acceptable salt, solvate, polymorph, ester, tautomer or pro-drug thereof.

In other aspects, the present invention is directed to a method of treating an inflammatory disease, condition, or disorder in a mammal, including a human, comprising administering to said mammal a therapeutically effective amount of a compound of formula I or formula II, or a pharmaceutically acceptable salt, ester, prodrug, solvate, such as hydrate, polymorph or tautomer thereof.

In other aspects, the present invention is directed to a method of treating a disorder or condition which is modulated by the MEK cascade in a mammal, including a human, comprising administering to said mammal an amount of the compound of formula I or formula II, or a pharmaceutically acceptable salt, ester, prodrug, solvate, such as hydrate, polymorph or tautomer thereof, effective to modulate said cascade. The appropriate dosage for a particular patient can be determined, according to known methods, by those skilled in the art.

In other aspects, the present invention is directed to use of compound of formula I or formula II or a pharmaceutically acceptable salt, ester, prodrug, solvate, such as hydrate, polymorph or tautomer thereof in the preparation of a pharmaceutical composition. The pharmaceutical composition can be used for treating a disorder or condition which is modulated by the MEK cascade in a mammal, including a human. The pharmaceutical composition is useful for treating cancer, inflammatory disease and other hyperproliferative diseases.

In other aspects, the present invention is directed to a pharmaceutical composition comprising a compound of formula I or formula II or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution and suspension. In some embodiments, the pharmaceutical composition is in a form suitable for parenteral injection, such as a sterile solution, suspension or emulsion; for topical administration as an ointment or cream or for rectal administration as a suppository. In further or additional embodiments, the pharmaceutical composition is in unit dosage forms suitable for single administration of precise dosages. In further or additional embodiments the amount of compound of formula I or formula II is in the range of about 0.001 to about 1000 mg/kg body weight/day. In further or additional embodiments the amount of compound of formula I or formula II is in the range of about 0.5 to about 50 mg/kg body weight/day. In further or additional embodiments the amount of compound of formula I or formula II is about 0.001 to about 7 g/day. In further or additional embodiments the amount of compound of formula I or formula II is about 0.002 to about 6 g/day. In further or additional embodiments the amount of compound of formula I or formula II is about 0.005 to about 5 g/day. In further or additional embodiments the amount of compound of formula I or formula II is about 0.01 to about 5 g/day. In further or additional embodiments the amount of compound of formula I or formula II is about 0.02 to about 5 g/day. In further or additional embodiments the amount of compound of formula I or formula II is about 0.05 to about 2.5 g/day. In further or additional embodiments the amount of compound of formula I or formula II is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I or formula II is administered in a single dose, once daily. In further or additional embodiments the compound of formula I or formula II is administered in multiple doses, more than once per day. In further or additional embodiments the compound of formula I or formula II is administered twice daily. In further or additional embodiments the compound of formula I or formula II is administered three times per day. In further or additional embodiments the compound of formula I or formula II is administered four times per day. In further or additional embodiments the compound of formula I or formula II is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition further comprises at least one therapeutic agent. In further or additional embodiments, the therapeutic agent is selected from the group consisting of cytotoxic agents, anti-angiogenesis agents and anti-neoplastic agents. In further or additional embodiments, the anti-neoplastic agent is selected from the group consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy or a combination of both. In further or additional embodiments, the pharmaceutical composition comprises a pharmaceutically acceptable salt of a compound of formula I or formula II.

In other aspects, the present invention is directed to a method for inhibiting a MEK enzyme. The method comprises contacting said MEK enzyme with an amount of a composition comprising a compound of formula I formula II or a pharmaceutically acceptable salt, solvate, polymorph, ester, tautomer or prodrug thereof, sufficient to inhibit said enzyme, wherein said enzyme is inhibited. In some embodiments, the present invention is directed to a method for selectively inhibiting a MEK enzyme.

In other aspects, the present invention is directed to use of a compound of formula I or formula II or a pharmaceutically acceptable salt, solvate, polymorph, ester, tautomer or prodrug thereof in the preparation of a pharmaceutical composition for inhibiting a MEK enzyme.

In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited. In further or additional embodiments the MEK enzyme is MEK kinase. In further or additional embodiments the MEK enzyme is MEK1. In further or additional embodiments the MEK enzyme is MEK2. In some embodiments, the compounds of this invention can selectively inhibit a MEK1 enzyme or MEK2 enzyme. In some other embodiments, the compounds of this invention may not have a selectivity between a MEK1 enzyme and MEK2 enzyme. In further or additional embodiments the contacting occurs within a cell. In further or additional embodiments the cell is a mammalian cell. In further or additional embodiments the mammalian cell is a human cell. In further or additional embodiments, the MEK enzyme is inhibited with a composition comprising a pharmaceutically acceptable salt of a compound of formula I or formula II.

In other aspects, the present invention is directed to a method of treatment of a MEK mediated disorder in an individual suffering from said disorder comprising administering to said individual an effective amount of a composition comprising a compound of formula I or formula II or a pharmaceutically acceptable salt, solvate, polymorph, ester, tautomer or prodrug thereof.

In other aspects, the present invention is directed to use of a compound of formula I or formula II or a pharmaceutically acceptable salt, solvate, polymorph, ester, tautomer or prodrug thereof in the preparation of a pharmaceutical composition for treating a MEK mediated disorder.

In some embodiments, the composition comprising a compound of formula I or formula II is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution and suspension for oral administration, for parenteral injection as a sterile solution, suspension or emulsion, for topical administration as an ointment or cream, or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant. In further or additional embodiments the amount of compound of formula I or formula II is in the range of about 0.001 to about 1000 mg/kg body weight/day. In further or additional embodiments the amount of compound of formula I or formula II is in the range of about 0.5 to about 50 mg/kg body weight/day. In further or additional embodiments the amount of compound of formula I or formula II is about 0.001 to about 7 g/day. In further or additional embodiments the amount of compound of formula I or formula II is about 0.01 to about 7 g/day. In further or additional embodiments the amount of compound of formula I or formula II is about 0.02 to about 5 g/day. In further or additional embodiments the amount of compound of formula I or formula II is about 0.05 to about 2.5 g/day. In further or additional embodiments the amount of compound of formula I or formula II is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I or formula II is administered in a single dose, once daily. In further or additional embodiments the compound of formula I or formula II is administered in multiple doses, more than once per day. In further or additional embodiments the compound of formula I or formula II is administered twice daily. In further or additional embodiments the compound of formula I or formula II is administered three times per day. In further or additional embodiments the compound of formula I or formula II is administered four times per day. In further or additional embodiments the compound of formula I or formula II is administered more than four times per day. In some embodiments, the individual suffering from the MEK mediated disorder is a mammal. In further or additional embodiments, the individual is a human. In some embodiments, the composition comprising a compound of formula I or formula II is administered in combination with an additional therapy. In further or additional embodiments, the additional therapy is radiation therapy, chemotherapy or a combination of both. In further or additional embodiments, the composition comprising a compound of formula I or formula II is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, antimetabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the MEK mediated disorder is selected from the group consisting of inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma. In further or additional embodiments, the MEK mediated disorder is an inflammatory disease. In further or additional embodiments, the MEK mediated disorder is a hyperproliferative disease. In further or additional embodiments, the MEK mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of formula I or formula II is administered.

In other aspects, the present invention is directed to a method for degrading, inhibiting the growth of or killing a cancer cell comprising contacting said cell with an amount of a composition effective to degrade, inhibit the growth of or to kill said cell, the composition comprising a compound of formula I or formula II or a pharmaceutically acceptable salt, solvate, polymorph, ester, tautomer or prodrug thereof.

In other aspects, the present invention is directed to use of a compound of formula I or formula II or a pharmaceutically acceptable salt, solvate, polymorph, ester, tautomer or prodrug thereof in the preparation of a pharmaceutical composition for degrading and/or inhibiting the growth of or killing a cancer cell.

In some embodiments, the cancer cells comprise brain, breast, lung, ovarian, pancreatic, prostate, renal, or colorectal cancer cells. In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded. In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed. In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In further or additional embodiments, a composition comprising a pharmaceutically acceptable salt of a compound of formula I or formula II is used.

In other aspects, the present invention is directed to a method for the treatment or prophylaxis of a proliferative disease in an individual comprising administering to said individual an effective amount of a composition comprising a compound of formula I or formula II or a pharmaceutically acceptable salt, solvate, polymorph, ester, tautomer or prodrug thereof.

In other aspects, the present invention is directed to use of a compound of formula I or formula II or a pharmaceutically acceptable salt, solvate, polymorph, ester, tautomer or prodrug thereof in the preparation of a pharmaceutical composition for the treatment or prophylaxis of a proliferative disease.

In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I or formula II is administered in combination with an additional therapy. In further or additional embodiments, the additional therapy is radiation therapy, chemotherapy or a combination of both. In further or additional embodiments, the composition comprising a compound of formula I or formula II is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I or formula II is in the range of about 0.001 to about 1000 mg/kg body weight/day. In further or additional embodiments the amount of compound of formula I or formula II is in the range of about 0.5 to about 50 mg/kg body weight/day. In further or additional embodiments the amount of compound of formula I or formula II is about 0.001 to about 7 g/day. In further or additional embodiments the amount of compound of formula I or formula II is about 0.01 to about 7 g/day. In further or additional embodiments the amount of compound of formula I or formula II is about 0.02 to about 5 g/day. In further or additional embodiments the amount of compound of formula I or formula II is about 0.05 to about 2.5 g/day. In further or additional embodiments the amount of compound of formula I or formula II is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I or formula II is administered in a single dose, once daily. In further or additional embodiments the compound of formula I or formula II is administered in multiple doses, more than once per day. In further or additional embodiments the compound of formula I or formula II is administered twice daily. In further or additional embodiments the compound of formula I or formula II is administered three times per day. In further or additional embodiments the compound of formula I or formula II is administered four times per day. In further or additional embodiments the compound of formula I or formula II is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of formula I or formula II is administered.

In other aspects, the present invention is directed to a method for the treatment or prophylaxis of an inflammatory disease in an individual comprising administering to said individual an effective amount of a composition comprising a compound of formula I or formula II or a pharmaceutically acceptable salt, solvate, polymorph, ester, tautomer or prodrug thereof.

In other aspects, the present invention is directed to use of a compound of formula I or formula II or a pharmaceutically acceptable salt, solvate, polymorph, ester, tautomer or prodrug thereof in the preparation of a pharmaceutical composition for the treatment or prophylaxis of an inflammatory disease.

In further or additional embodiments, the inflammatory disease is selected from chronic inflammatory diseases, rheumatoid arthritis, spondyloarthropathies, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma. In some embodiments, the composition comprising a compound of formula I or formula II is administered in combination with an additional therapy. In further or additional embodiments, the composition comprising a compound of formula I or formula II is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I or formula II is in the range of about 0.001 to about 1000 mg/kg body weight/day. In further or additional embodiments the amount of compound of formula I or formula II is in the range of about 0.5 to about 50 mg/kg body weight/day. In further or additional embodiments the amount of compound of formula I or formula II is about 0.001 to about 7 g/day. In further or additional embodiments the amount of compound of formula I or formula II is about 0.01 to about 7 g/day. In further or additional embodiments the amount of compound of formula I or formula II is about 0.02 to about 5 g/day. In further or additional embodiments the amount of compound of formula I or formula II is about 0.05 to about 2.5 g/day. In further or additional embodiments the amount of compound of formula I or formula II is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I or formula II is administered in a single dose, once daily. In further or additional embodiments the compound of formula I or formula II is administered in multiple doses, more than once per day. In further or additional embodiments the compound of formula I or formula II is administered twice daily. In further or additional embodiments the compound of formula I or formula II is administered three times per day. In further or additional embodiments the compound of formula I or formula II is administered four times per day. In further or additional embodiments the compound of formula I or formula II is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of formula I or formula II is administered.

In other aspects, the present invention is directed to a method for the treatment or prophylaxis of cancer in an individual comprising administering to said individual an effective amount of a composition comprising a compound of formula I or formula II or a pharmaceutically acceptable salt, solvate, polymorph, ester, tautomer or prodrug thereof.

In other aspects, the present invention is directed to use of a compound of formula I or formula II or a pharmaceutically acceptable salt, solvate, polymorph, ester, tautomer or prodrug thereof in the preparation of a pharmaceutical composition for the treatment or prophylaxis of a cancer.

In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I or formula II is administered in combination with an additional therapy. In further or additional embodiments, the additional therapy is radiation therapy, chemotherapy or a combination of both. In further or additional embodiments, the composition comprising a compound of formula I or formula II is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, antimetabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I or formula II is in the range of about 0.001 to about 1000 mg/kg body weight/day. In further or additional embodiments the amount of compound of formula I or formula II is in the range of about 0.5 to about 50 mg/kg body weight/day. In further or additional embodiments the amount of compound of formula I or formula II is about 0.001 to about 7 g/day. In further or additional embodiments the amount of compound of formula I or formula II is about 0.01 to about 7 g/day. In further or additional embodiments the amount of compound of formula I or formula II is about 0.02 to about 5 g/day. In further or additional embodiments the amount of compound of formula I or formula II is about 0.05 to about 2.5 g/day. In further or additional embodiments the amount of compound of formula I or formula II is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I or formula II is administered in a single dose, once daily. In further or additional embodiments the compound of formula I or formula II is administered in multiple doses, more than once per day. In further or additional embodiments the compound of formula I or formula II is administered twice daily. In further or additional embodiments the compound of formula I or formula II is administered three times per day. In further or additional embodiments the compound of formula I or formula II is administered four times per day. In further or additional embodiments the compound of formula I or formula II is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I or formula II is administered.

In other aspects, the present invention is directed to a method of reducing the size of a tumor, inhibiting tumor size increase, reducing tumor proliferation or preventing tumor proliferation in an individual, comprising administering to said individual an effective amount of a composition comprising a compound of formula I or formula II or a pharmaceutically acceptable salt, solvate, polymorph, ester, tautomer or prodrug thereof.

In other aspects, the present invention is directed to use of a compound of formula I or formula II or a pharmaceutically acceptable salt, solvate, polymorph, ester, tautomer or prodrug thereof in the preparation of a pharmaceutical composition for reducing the size of a tumor, inhibiting tumor size increase, reducing tumor proliferation or preventing tumor proliferation.

In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase. In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented. In some embodiments, the composition comprising a compound of formula I or formula II is administered in combination with an additional therapy. In further or additional embodiments, the additional therapy is radiation therapy, chemotherapy or a combination of both. In further or additional embodiments, the composition comprising a compound of formula I or formula II is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I or formula II is in the range of about 0.001 to about 1000 mg/kg body weight/day. In further or additional embodiments the amount of compound of formula I or formula II is in the range of about 0.5 to about 50 mg/kg body weight/day. In further or additional embodiments the amount of compound of formula I or formula II is about 0.001 to about 7 g/day. In further or additional embodiments the amount of compound of formula I or formula II is about 0.01 to about 7 g/day. In further or additional embodiments the amount of compound of formula I or formula II is about 0.02 to about 5 g/day. In further or additional embodiments the amount of compound of formula I or formula II is about 0.05 to about 2.5 g/day. In further or additional embodiments the amount of compound of formula I or formula II is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I or formula II is administered in a single dose, once daily. In further or additional embodiments the compound of formula I or formula II is administered in multiple doses, more than once per day. In further or additional embodiments the compound of formula I or formula II is administered twice daily. In further or additional embodiments the compound of formula I or formula II is administered three times per day. In further or additional embodiments the compound of formula I or formula II is administered four times per day. In further or additional embodiments the compound of formula I or formula II is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I or formula II is administered.

In other aspects, the present invention is directed to a method for achieving an effect in a patient comprising the administration of an effective amount of a composition comprising a compound of formula I or formula II or a pharmaceutically acceptable salt, solvate, polymorph, ester, tautomer or prodrug thereof, to a patient, wherein the effect is selected from the group consisting of inhibition of various cancers, immunological diseases, and inflammatory diseases. In some embodiments, the effect is inhibition of various cancers. In further or additional embodiments, the effect is inhibition of immunological diseases. In further or additional embodiments, the effect is inhibition inflammatory diseases.

In other aspects, the present invention is directed to use of a compound of formula I or formula II or a pharmaceutically acceptable salt, solvate, polymorph, ester, tautomer or prodrug thereof in the preparation of a pharmaceutical composition for the inhibiting various cancers, immunological diseases, and/or inflammatory diseases.

In some embodiments, the composition comprising a compound of formula I or formula II is administered in combination with an additional therapy. In further or additional embodiments, the additional therapy is radiation therapy, chemotherapy or a combination of both. In further or additional embodiments, the composition comprising a compound of formula I or formula II is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I or formula II is in the range of about 0.001 to about 1000 mg/kg body weight/day. In further or additional embodiments the amount of compound of formula I or formula II is in the range of about 0.5 to about 50 mg/kg body weight/day. In further or additional embodiments the amount of compound of formula I or formula II is about 0.001 to about 7 g/day. In further or additional embodiments the amount of compound of formula I or formula II is about 0.01 to about 7 g/day. In further or additional embodiments the amount of compound of formula I or formula II is about 0.02 to about 5 g/day. In further or additional embodiments the amount of compound of formula I or formula II is about 0.05 to about 2.5 g/day. In further or additional embodiments the amount of compound of formula I or formula II is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I or formula II is administered in a single dose, once daily. In further or additional embodiments the compound of formula I or formula II is administered in multiple doses, more than once per day. In further or additional embodiments the compound of formula I or formula II is administered twice daily. In further or additional embodiments the compound of formula I or formula II is administered three times per day. In further or additional embodiments the compound of formula I or formula II is administered four times per day. In further or additional embodiments the compound of formula I or formula II is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I or formula II is administered.

In other aspects, the present invention is directed to a process for preparing a compound of formula I or formula II or a pharmaceutically acceptable salt, solvate, polymorph, ester, tautomer or prodrug thereof.

The compounds provided can be used as inhibitors of MEK and are useful in the treatment of inflammatory diseases, cancer and other hyperproliferative diseases. Also, the method of this invention can be used to treat inflammatory diseases, cancer and other hyperproliferative diseases in mammals, especially humans.

DETAILED DESCRIPTION

Figure 1:
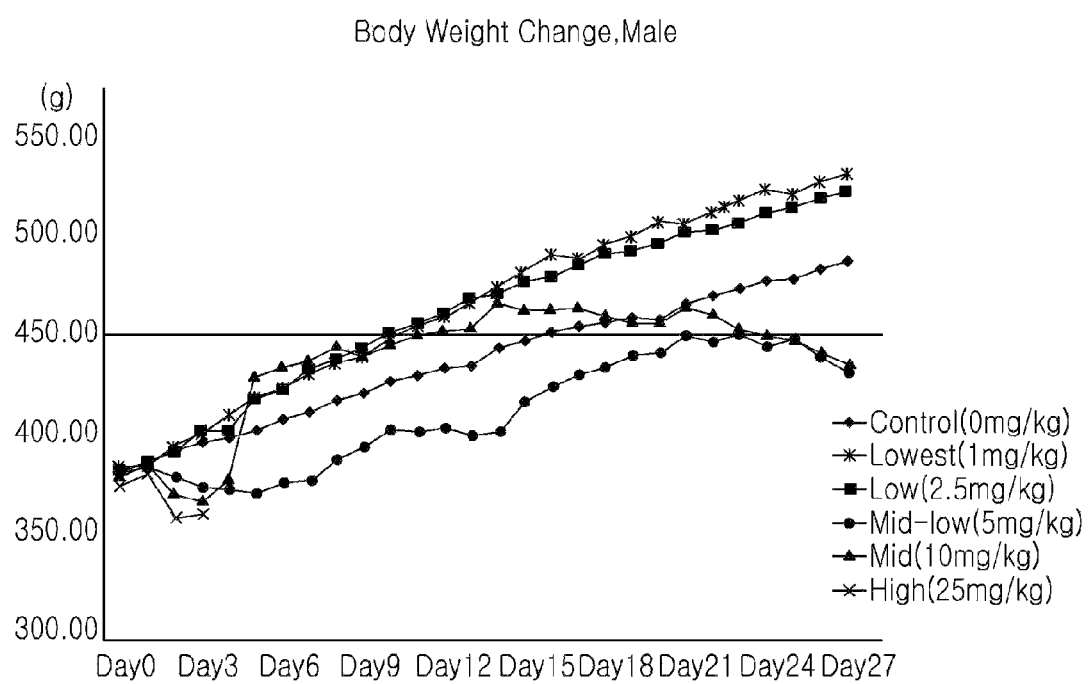
FIG. 1 shows the change in body weight in the male (data of CZ3113).

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

CERTAIN CHEMICAL TERMINOLOGY

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4TH ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., $CH_2CH_3$), fully substituted (e.g., $CF_2CF_3$), mono-substituted (e.g., $CH_2CH_2F$) or substituted at a level anywhere in-between fully substituted and mono-substituted (e.g., $CH_2CHF_2$, $CF_2CH_3$, $CFHCHF_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_n$, includes $C_1$-$C_2$, $C_1$-$C_3$, . . . $C_1$-$C_n$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon and hydrogen. Heteroatoms are independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkylene" as used herein, alone or in combination, refers to a diradical derived from the above defined monoradical, alkyl. Examples include, but are not limited to methylene (—$CH_2$—), ethylene (—$CH_2CH_2$—), propylene (—$CH_2CH_2CH_2$—), isopropylene (—$CH(CH_3)CH_2$—) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl ($CH$=$CH_2$), 1-propenyl ($CH_2CH$=$CH_2$), isopropenyl [$C(CH_3)$=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkynyl" as used herein, alone or in combination, refers to an optionally substituted straight-chain or optionally substituted branched-chain hydrocarbon mono-radical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl).

A non-limiting example of "cycloalkyl" includes azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl and quinolizinyl and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized $\pi$-electron system containing $4n+2$ $\pi$ electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic mono-radicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide and the like.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom. The term "alkoxy" as used herein, alone or in combination, refers to an alkyl ether radical, O-alkyl, including the groups O-aliphatic and O-carbocycle, wherein the alkyl, aliphatic and carbocycle groups may be optionally substituted, and wherein the terms alkyl, aliphatic and carbocycle are as defined herein. Non-limiting examples of alkoxy radicals include methoxy, ethoxy, n-propoxy, iso-propoxy, n-butoxy, iso-butoxy, sec-butoxy, tertbutoxy and the like.

CERTAIN PHARMACEUTICAL TERMINOLOGY

The term "MEK inhibitor" as used herein refers to a compound that exhibits an $IC_{50}$, with respect to MEK activity, of no more than about 100 µM or not more than about 50 µM, as measured in the Mek1 kinase assay described generally herein. "$IC_{50}$" is that concentration of inhibitor which reduces the activity of an enzyme (e.g., MEK) to half-maximal level. Compounds described herein have been discovered to exhibit inhibition against MEK. Compounds of the present invention preferably exhibit an $IC_{50}$ with respect to MEK of no more than about 10 µM, more preferably, no more than about 5 µM, even more preferably not more than about 1 µM, and most preferably, not more than about 200 nM, as measured in the Mek1 kinase assay described herein.

The term "selective," "selectively," or "selectivity" as used herein refers to a compound of this invention having a lower $IC_{50}$ value for a MEK enzyme as compared to any other enzymes (e.g., at least 2, 5, 10 or more-fold lower). The term may also refer to a compound of this invention having a lower $IC_{50}$ value for a MEK1 enzyme as compared to a MEK2 enzyme (e.g., at least 2, 5, 10 or more-fold) or alternatively having a lower $IC_{50}$ value for a MEK2 enzyme as compared to a MEK1 enzyme (e.g., at least 2, 5, 10 or more-fold lower).

The term "subject", "patient" or "individual" as used herein in reference to individuals suffering from a disorder, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfate, bromide, butyrate, butyn-1,4-dioate, camphorate, camphorsulfonate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts (See examples at Berge et al., J. Pharm. Sci. 1977, 66, 1-19). Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $IV'$ $(C_{1-4}$ alkyl$)_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra.

The term "solvate" as used herein refers to a combination of a compound of this invention with a solvent molecule formed by solvation. In some situations, the solvate refers to a hydrate, i.e., the solvent molecule is a water molecule, the combination of a compound of this invention and water forms a hydrate.

The term "polymorph" or "polymorphism" as used herein refers to a compound of this invention present in different crystal lattice forms.

The term "ester" as used herein refers to a derivative of a compound of this invention derived from an oxoacid group and a hydroxyl group, either one of which can be present at the compound of this invention.

The term "tautomer" as used herein refers to an isomer readily interconverted from a compound of this invention by e.g., migration of a hydrogen atom or proton.

The term "pharmaceutically acceptable derivative or prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. The prodrugs described herein include, but are not limited to, the following groups and combinations of these groups; amine derived prodrugs: Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996).

EXAMPLES

Synthetic Procedures and Examples

The Preparation of Compounds of Formula I is Outlined Below:

Scheme 1

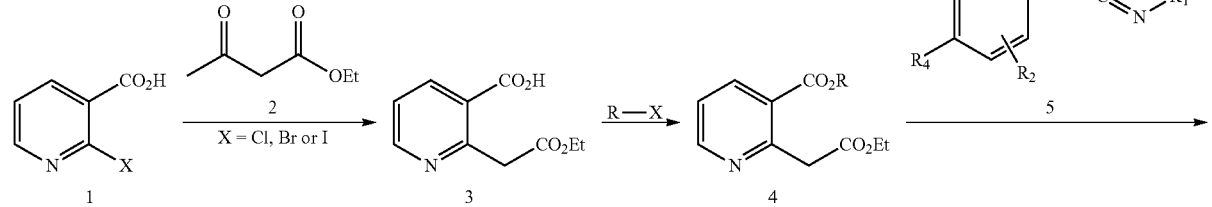

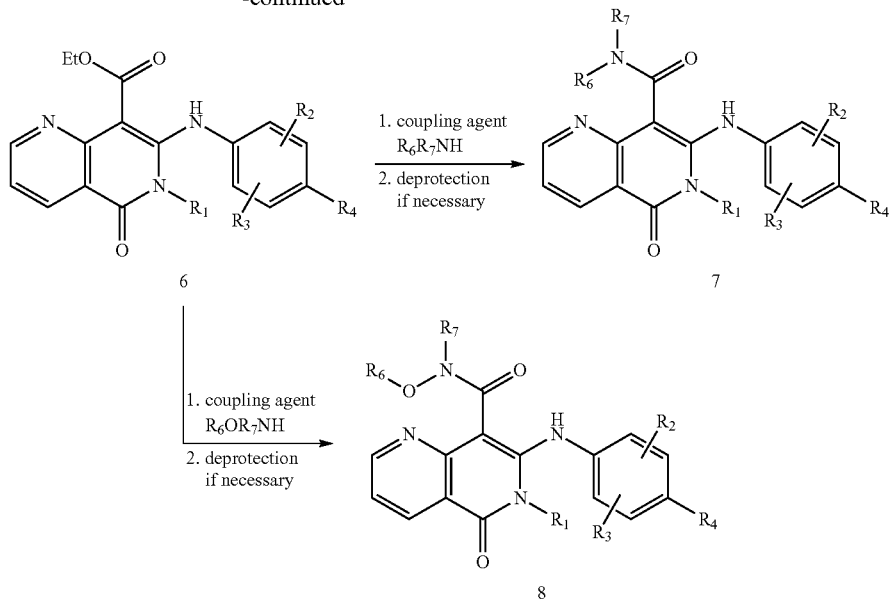

Scheme 1 illustrates synthesis of compounds of Formula I. Condensation reaction of o-halogenopridinecarboxylic acid (1) with ethyl acetoacetate (2) gives the pyridylacetate intermediate (3). Ester 4 can be prepared by standard conditions in suitable organic solvent. Condensation with iminoaniline derivatives (5) affords the pyridone (6). This can be done in a suitable organic solvent such as THF using a base such as NaH or LiH at appropriate temperatures (0° C. to room temperature). Amides (7) and hydroxamates (8) can be prepared with the amine or hydroxylamine neat at elevated temperature by microwave irradiation. In some instances, the amine or hydroxylamine used in the coupling reaction conditions a standard protecting group. In those cases, the protecting group can be removed by standard conditions known in the art.

The iminoaniline derivatives (5) can be prepared in two steps from anilines by coupling to form the urea followed by reaction with carbon tetrabromide and triphenylphosphine to afford intermediates (5) [Scheme 2].

The Preparation of Compounds of Formula II is Outlined Below:

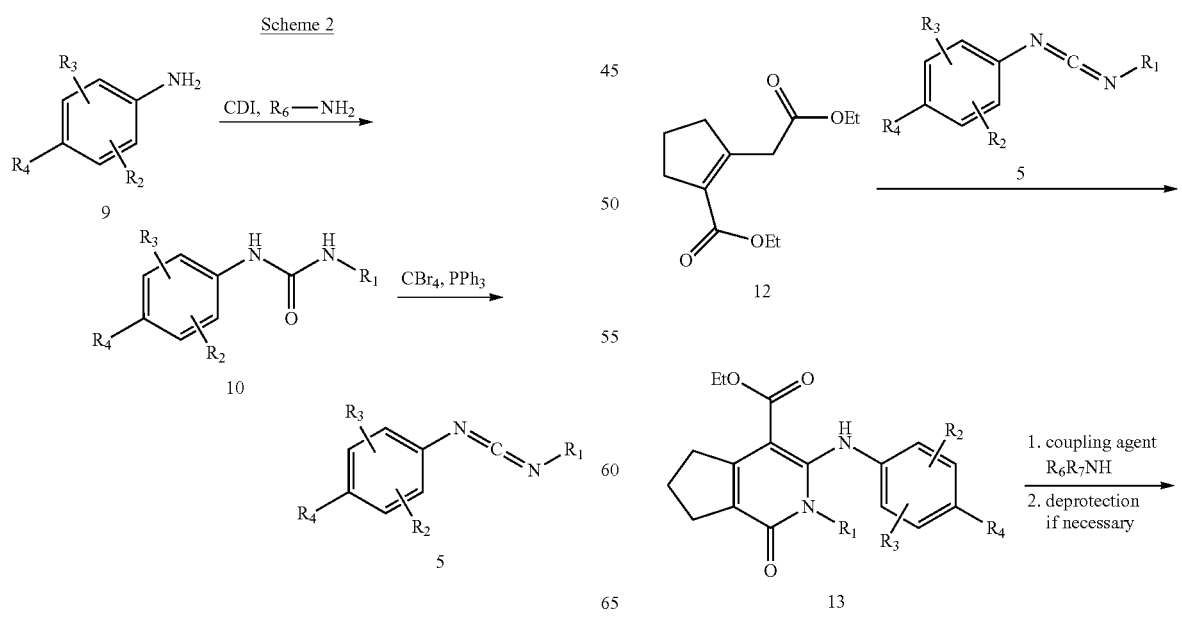

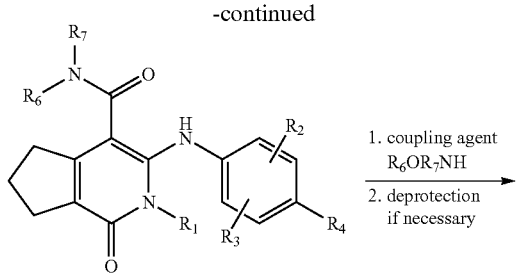

14

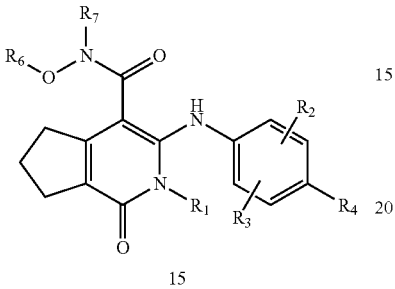

15

Scheme 3 illustrates synthesis of compounds of Formula II. Addition of the phosphonium bromide to the carbonyl group (11) affords the unsaturated ester (12) according to the general methods described by Luca Guandalini et al., Helvetica Chimica Acta 85, 2002, 96-107. The unsaturated ester (12) can be converted to bicyclic pyridone (13) as described in Scheme 1. Amide (14) or hydroxamate (15) can be prepared by treating pyridone ester (13) with the appropriate hydroxylamine and amide base such as LDA, LiHMDS or NaHMDS in a suitable organic solvent such as THF at low temperature.

Intermediate 1

2-fluoro-4-iodo-N-((methylimino)methylene)aniline

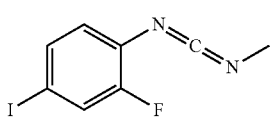

Step A: 1-(2-fluoro-4-iodophenyl)-3-methylurea

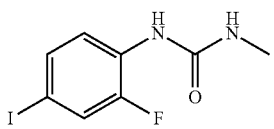

To N,N'-carbonyldiimidazole (51.3 g, 316 mmol) in dry DMF (52 mL) was added TEA (3.55 mL, 25.5 mmol) after addition of a solution of 2-fluoro-4-iodoaniline (50.0 g, 211 mmol) in dry DMF (52 mL) at 0° C. under a $N_2$ atmosphere. The reaction mixture was stirred at room temperature for 16 h followed by the addition of a solution of methylamine (40% in water, 24.5 g, 316 mmol) at 0° C. After stirring for 1 h at room temperature, the reaction mixture was added to water/toluene (v/v=2/1) while stirring. The resulting solid was collected by filtration, rinsed with water and dried in vacuo to give 1-(2-fluoro-4-iodophenyl)-3-methylurea (57.6 g, 93%) as a white solid, which was used for the next reaction without further purification. $^1$H NMR (DMSO-$d_6$, Varian 400 MHz) δ 2.64 (3H, d, J=2.4 Hz), 6.45-6.49 (1H, m), 7.40-7.42 (1H, m), 7.55 (1H, dd, J=5.4, 2.0 Hz), 7.95 (1H, t, J=8.8 Hz), 8.36 (1H, brs).

Step B:
2-fluoro-4-iodo-N-((methylimino)methylene)aniline

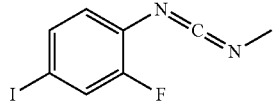

To a solution of 1-(2-fluoro-4-iodophenyl)-3-methylurea (15.0 g, 51.0 mmol) and TEA (28.3 mL, 204 mmol) in DCM (250 mL) was added $CBr_4$ (33.8 g, 102 mmol) and $PPh_3$ (26.8 g, 102 mmol) at room temperature. The reaction mixture was stirred at room temperature for 4 h. The mixture solvent was concentrated under reduce pressure and the residue purified by flash column chromatography on $SiO_2$ (Hex:EtOAc=20:1 to 5:1) to give 2-fluoro-4-iodo-N-((methylimino)methylene)aniline (9.00 g, 64%) as a red oil. $^1$H NMR (CDCl$_3$, Varian 400 MHz) δ 3.17 (3H, s), 6.78 (1H, t, J=8.4 Hz), 7.33-7.36 (1H, m), 7.38-7.41 (1H, m).

Intermediate 2

O-(2-(tert-butyldimethylsilyloxy)ethyl)hydroxylamine

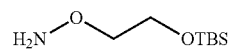

Step A: 2-(tert-butyldimethylsilyloxy)ethanol

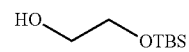

A mixture of ethane-1,2-diol (3.71 mL, 66.3 mmol) and imidazole (4.52 g, 66.3 mmol) in THF (20 mL) was added tert-butyldimethylchlorosilane (5.0 g, 33.5 mmol) at stirred 0° C. After stirring overnight at room temperature, the reaction mixture was partitioned between EtOAc and saturated aq. $NH_4Cl$. The separated organic layer was washed with water and brine, dried over $Na_2SO_4$, filtered and concentrated in vacuo. The residue was purified by column chromatography on $SiO_2$ (Hex: EtOAc=4:1) to give 2-(tert-butyldimethylsilyloxy)ethanol (3.32 g, 57%) as a colorless oil. $^1$H NMR (CDCl$_3$, Varian 400 MHz) δ 0.09 (6H, s), 0.91 (9H, s), 2.09 (1H, t, J=5.6 Hz), 3.62-3.66 (2H, m), 3.70-3.73 (2H, m).

Step B: 2-(2-(tert-butyldimethylsilyloxy)ethoxy)isoindoline-1,3-dione

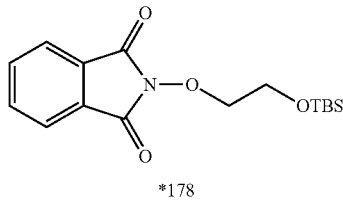 [SMILES: CC(C)(C)[Si](C)(C)OCCON1C(=O)c2ccccc2C1=O]

*178

To a solution of 2-(tert-butyldimethylsilyloxy)ethanol (3.32 g, 18.8 mmol), triphenylphosphine (4.94 g, 18.8 mmol), and N-hydroxyphthalimide (3.07 g, 18.8 mmol) in THF (40 mL) was added DEAD (2.98 mL, 18.8 mmol) at 0° C. under a $N_2$ atmosphere. After stirring overnight at room temperature, the reaction mixture was concentrated in vacuo. The residue was filtered, washed with chloroform and the filtrate was concentrated in vacuo. The residue was purified by column chromatography on $SiO_2$ (Hex:EtOAc=9:1) to give 2-(2-(tert-butyldimethylsilyloxy)ethoxy)isoindoline-1,3-dione (4.30 g, 71%) as a white solid. $^1$H NMR (CDCl$_3$, Varian 400 MHz) δ 0.02 (6H, s), 0.81 (9H, s), 3.99-4.01 (2H, m), 4.29-4.32 (2H, m), 7.73-7.76 (2H, m), 7.81-7.84 (2H, m).

Step C: O-(2-(tert-butyldimethylsilyloxy)ethyl)hydroxylamine

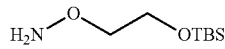

To a solution of 2-(2-(tert-butyldimethylsilyloxy)ethoxy)isoindoline-1,3-dione (4.30 g, 13.4 mmol) in DCM (10 mL) was added dropwise an aqueous solution of methylhydrazine (1.54 mL, 13.4 mmol) at room temperature. After being stirred for 1 h at room temperature, the suspension was diluted with diethyl ether and filtered. The filtrate was concentrated in vacuo. The residue was purified by column chromatography on $SiO_2$ (Hex:EtOAc=4:1 to 7:3) to give O-(2-(tert-butyldimethylsilyloxy)ethyl)hydroxylamine (2.37 g, 92%) as a colorless oil. $^1$H NMR (CDCl$_3$, Varian 400 MHz) δ 0.86 (6H, s), 0.91 (9H, s), 2.09 (1H, t, J=5.6 Hz), 3.62-3.66 (2H, m), 3.70-3.73 (2H, m).

Intermediate 3

(S)—O-(2-(tert-butyldimethylsilyloxy)propyl)hydroxylamine

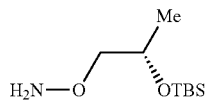

Step A: (S)-ethyl 2-(tert-butyldimethylsilyloxy)propanoate

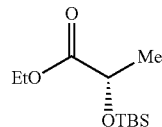

To a solution of (S)-ethyl 2-hydroxypropanoate (10.0 g, 85.0 mmol) in DCM (56 mL) was added imidazole (6.92 g, 102 mmol) and TBS-Cl (13.4 g, 89.0 mmol) at 0° C. After being stirred at room temperature for 2 hours, the reaction was diluted with water and extracted with EtOAc. The organic layer was washed with brine, dried and concentrated in vacuo to give (S)-ethyl 2-(tert-butyldimethylsilyloxy)propanoate (19.6 g, 100%) as a colourless oil. $^1$H-NMR (CDCl$_3$, Varian, 400 MHz): δ 0.07 (3H, s), 0.10 (3H, s), 0.90 (9H, s), 1.28 (3H, t, J=7.2 Hz), 1.40 (3H, d, J=6.8 Hz), 4.13-4.22 (2H, m), 4.31 (1H, q, J=6.4 Hz).

Step B: (S)-2-(tert-butyldimethylsilyloxy)propan-1-ol

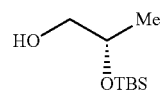

To a mixture of (S)-ethyl 2-(tert-butyldimethylsilyloxy)propanoate (19.6 g, 84.0 mmol) and MeOH (4.44 mL, 110 mmol) in diethyl ether (450 mL) was added LiBH$_4$ (3 M in THF, 36.5 mL, 110 mmol) at 0° C. After being stirred for 2 hours at room temperature, the mixture was cooled to 0° C., quenched with water (carefully), and extracted with diethyl ether. The organic layer was washed with brine, dried and concentrated in vacuo to give (S)-2-(tert-butyldimethylsilyloxy)propan-1-ol (15.5 g, 97%) as a colourless oil. $^1$H-NMR (CDCl$_3$, Varian, 400 MHz): δ 0.00 (6H, s), 0.81 (9H, s), 1.03 (3H, d, J=8.4 Hz), 1.83-1.86 (1H, m), 3.25-3.30 (1H, m), 3.39-3.44 (1H, m), 3.79-3.86 (1H, m).

Step C: 2(S)-2-(2-(tert-butyldimethylsilyloxy)propoxy)isoindoline-1,3-dione

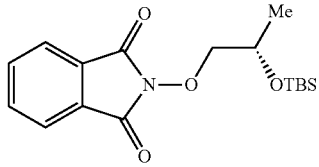 [SMILES: C[C@@H](CON1C(=O)c2ccccc2C1=O)O[Si](C)(C)C(C)(C)C]

To a solution of (S)-2-(tert-butyldimethylsilyloxy)propan-1-ol (15.5 g, 81.0 mmol), triphenylphosphine (21.36 g, 81.0 mmol), and N-hydroxyphthalimide (13.3 g, 81.0 mmol) in THF (163 mL) was added DIAD (15.83 mL, 81.0 mmol) at 0° C. under a $N_2$ atmosphere. After being stirred for 17 hours at room temperature, the mixture was concentrated in vacuo. The residue was diluted with chloroform, filtered and washed with chloroform, and then the filtrate was concentrated in vacuo. The residue was purified by column chromatography on SiO$_2$ (Hex: EtOAc=9:1) to give (S)-2-(2-(tert-butyldimethylsilyloxy)propoxy)isoindoline-1,3-dione (27.0 g, 99%) as a yellow solid. $^1$H-NMR (CDCl$_3$, Varian, 400 MHz): δ 0.09 (3H, s), 0.10 (3H, s), 0.88 (9H, s), 1.30 (3H, d, J=6.4 Hz), 4.02-4.05 (1H, m), 4.09-4.13 (1H, m), 4.18-4.23 (1H, m), 7.72-7.77 (2H, m), 7.81-7.85 (2H, m).

Step D: (S)—O-(2-(tert-butyldimethylsilyloxy)propyl)hydroxylamine

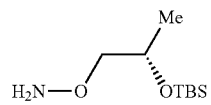

To a solution of (S)-2-(2-(tert-butyldimethylsilyloxy)propoxy)isoindoline-1,3-dione (27.3 g, 81.0 mmol) in DCM (54 mL) was added dropwise an aqueous solution of methylhydrazine (9.37 mL, 81.0 mmol) at 0° C. After being stirred for 1 hour at 0° C., the suspension was diluted with diethyl ether and filtered. The filtrate was concentrated in vacuo. The residue was purified by column chromatography on SiO$_2$ (Hex:EtOAc=4:1) to give (S)—O-(2-(tert-butyldimethylsilyloxy)propyl)hydroxylamine (9.60 g, 57%) as a colorless oil. $^1$H-NMR (CDCl$_3$, Varian, 400 MHz): δ 0.06 (6H, s), 0.90 (9H, s), 1.13 (3H, d, J=6.4 Hz), 3.50-3.54 (1H, m), 3.56-3.61 (1H, m), 4.01-4.07 (1H, m), 5.45 (2H, brs).

Intermediate 4

(R)—O-(2-(tert-butyldimethylsilyloxy)propyl)hydroxylamine

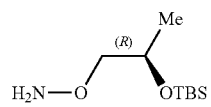

Step A: (R)-ethyl 2-(tert-butyldimethylsilyloxy)propanoate

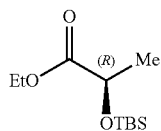

To a solution of (R)-ethyl 2-hydroxypropanoate (5.00 g, 42.3 mmol) in DCM (28.2 mL) was added imidazole (3.46 g, 50.8 mmol) and TBS-Cl (6.70 g, 44.4 mmol) at 0° C. After being stirred at room temperature for 3 hours, the reaction was diluted with water and extracted with EtOAc. The organic layer was washed with brine, dried and concentrated in vacuo to give (R)-ethyl 2-(tert-butyldimethylsilyloxy)propanoate (9.71 g, 99%) as a colourless oil.

$^1$H-NMR (CDCl$_3$, Varian, 400 MHz): δ 0.07 (3H, s), 0.10 (3H, s), 0.90 (9H, s), 1.28 (3H, t, J=7.0 Hz), 1.39 (3H, d, J=6.8 Hz), 4.11-4.26 (2H, m), 4.31 (1H, q, J=6.8 Hz).

Step B: (R)-2-(tert-butyldimethylsilyloxy)propan-1-ol

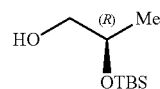

To a mixture of (R)-ethyl 2-(tert-butyldimethylsilyloxy)propanoate (1.00 g, 4.30 mmol) and MeOH (0.226 mL, 5.59 mmol) in diethyl ether (21 mL) was added LiBH$_4$ (3 M in THF) (1.87 mL, 5.59 mmol) at 0° C. After being stirred at room temperature for 2 hours, the reaction mixture was cooled to 0° C., carefully quenched with water, extracted with diethyl ether. The organic layer was washed with brine, dried and concentrated in vacuo to give (R)-2-(tert-butyldimethylsilyloxy)propan-1-ol (763 mg, 93%) as a yellow oil. $^1$H-NMR (CDCl$_3$, Varian, 400 MHz): δ 0.09 (6H, s), 0.91 (9H, s), 1.12 (3H, d, J=6.4 Hz), 1.91-1.95 (1H, m), 3.34-3.40 (1H, m), 3.48-3.53 (1H, m), 3.88-3.95 (1H, m).

Step C: (R)-2-(2-(tert-butyldimethylsilyloxy)propoxy)isoindoline-1,3-dione

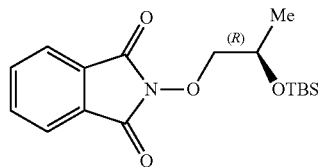

To a solution of (R)-2-(tert-butyldimethylsilyloxy)propan-1-ol (763 mg, 4.01 mmol), triphenylphosphine (1.05 g, 4.01 mmol), and N-hydroxyphthalimide (654 mg, 4.01 mmol) in THF (163 mL) was added DIAD (0.779 mL, 4.01 mmol) at 0° C. under a N$_2$ atmosphere. After being stirred at room temperature for 17 hours, the reaction mixture was concentrated in vacuo. The residue was filtered, washed with chloroform and the filtrate was concentrated in vacuo. The residue was purified by column chromatography on SiO$_2$ (Hex:EtOAc=9:1) to give (R)-2-(2-(tert-butyldimethylsilyloxy)propoxy)isoindoline-1,3-dione (814 mg, 61%) as a yellow solid. $^1$H-NMR (CDCl$_3$, Varian, 400 MHz): δ 0.09 (3H, s), 0.10 (3H, s), 0.88 (9H, s), 1.30 (3H, d, J=6.4 Hz), 4.02-4.05 (1H, m), 4.09-4.13 (1H, m), 4.18-4.23 (1H, m), 7.73-7.77 (2H, m), 7.81-7.85 (2H, m).

Step D: (R)—O-(2-(tert-butyldimethylsilyloxy)propyl)hydroxylamine

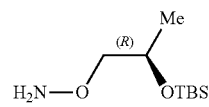

To a solution of (R)-2-(2-(tert-butyldimethylsilyloxy)propoxy)isoindoline-1,3-dione (814 mg, 2.43 mmol) in DCM (2.5 mL) was added dropwise an aqueous solution of methylhydrazine (0.307 mL, 2.67 mmol) at 0° C. After being stirred at 0° C. for 2 hour, the resulting suspension was diluted with diethyl ether and filtered. The filtrate was concentrated in vacuo. The residue was purified by column chromatography on SiO₂ (Hex:EtOAc=4:1) to give (R)—O-(2-(tert-butyldimethylsilyloxy)propyl)hydroxylamine (220 mg, 44%) as a colorless oil. ¹H-NMR (CDCl₃, Varian, 400 MHz): δ 0.08 (6H, s), 0.89 (9H, s), 1.13 (3H, d, J=6.0 Hz), 3.50-3.54 (1H, m), 3.56-3.61 (1H, m), 4.00-4.07 (1H, m), 5.45 (2H, brs).

Intermediate 5

O-(2-(tert-butyldimethylsilyloxy)-2-methylpropyl)hydroxylamine

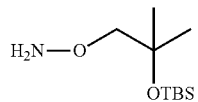

Step A:
2-(2-hydroxy-2-methylpropoxy)isoindoline-1,3-dione

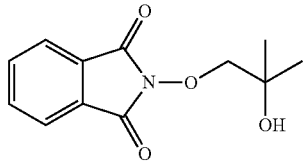 [SMILES: CC(C)(O)CON1C(=O)c2ccccc2C1=O]

To a solution of 2,2-dimethyloxirane (2.00 g, 27.7 mmol) and N-hydroxyphthalimide (5.43 g, 33.3 mmol) in DMF (56 mL) was added TEA (4.64 mL, 33.3 mmol) at room temperature under N₂ atmosphere. After being stirred at 85° C. for 17 hours, the reaction mixture was concentrated in vacuo. The mixture was partitioned between EtOAc and water. The separated organic layer was washed with water and brine, dried over anhydrous Na₂SO₄, filtered and concentrated in vacuo. The residue was purified by column chromatography on SiO₂ (Hex:EtOAc=2:1) to give 2-(2-hydroxy-2-methylpropoxy)isoindoline-1,3-dione (1.75 g, 27%) as a yellow solid. ¹H-NMR (CDCl₃, Varian, 400 MHz): δ 1.34 (6H, s), 4.11 (2H, s), 7.76-7.84 (2H, m), 7.85-7.86 (2H, m).

Step B: 2-(2-(tert-butyldimethylsilyloxy)-2-methylpropoxy)isoindoline-1,3-dione

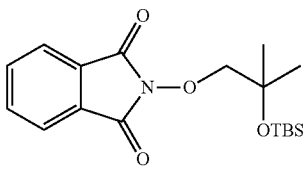 [SMILES: CC(C)(CON1C(=O)c2ccccc2C1=O)O[Si](C)(C)C(C)(C)C]

To a solution of 2-(2-hydroxy-2-methylpropoxy)isoindoline-1,3-dione (200 mg, 0.850 mmol) and 2,6-lutidine (0.198 mL, 1.70 mmol) in DCM (4 mL) was added tert-butyldimethylsilyl trifluoromethanesulfonate (0.293 mL, 1.28 mmol) at 0° C. After being stirred at room temperature for 3 hours, the reaction was diluted with water and extracted with EtOAc. The organic layer was washed with brine, dried and concentrated in vacuo. The residue was purified by column chromatography on SiO₂ (Hex:EtOAc=10:1) to give 2-(2-(tert-butyldimethylsilyloxy)-2-methylpropoxy)isoindoline-1,3-dione (295 mg, 99%) as a colorless oil. ¹H-NMR (CDCl₃, Varian, 400 MHz): δ 0.10 (6H, s), 0.84 (9H, s), 1.42 (6H, s), 3.99 (2H, s), 7.73-7.75 (2H, m), 7.82-7.84 (2H, m).

Step C: O-(2-(tert-butyldimethylsilyloxy)-2-methylpropyl)hydroxylamine

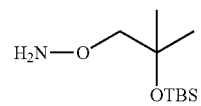

To a solution of 2-(2-(tert-butyldimethylsilyloxy)-2-methylpropoxy)isoindoline-1,3-dione (295 mg, 0.844 mmol) in DCM (1 mL) was added dropwise an aqueous solution of methylhydrazine (0.107 mL, 0.928 mmol) at 0° C. After being stirred at 0° C. for 5 hours, the suspension was diluted with diethyl ether and then filtered off. The filtrate was concentrated in vacuo. The residue was purified by column chromatography on SiO₂ (Hex:EtOAc=5:1) to give O-(2-(tert-butyldimethylsilyloxy)-2-methylpropyl)hydroxylamine (160 mg, 86%) as a colorless oil. ¹H-NMR (CDCl₃, Varian, 400 MHz): δ 0.09 (6H, s), 0.86 (9H, s), 1.20 (6H, s), 3.51 (2H, s), 5.53 (2H, brs).

Example 1

7-(2-fluoro-4-iodophenylamino)-N-(2-hydroxyethoxy)-6-methyl-5-oxo-5,6-dihydro-1,6-naphthyridine-8-carboxamide

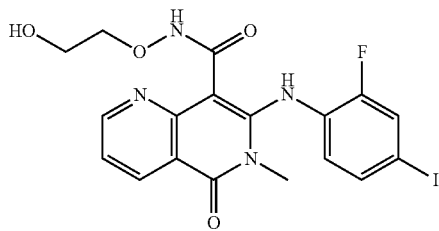 [SMILES: Cn1c(Nc2ccc(I)cc2F)c(C(=O)NOCCO)c2ncccc2c1=O]

Step A: 2-(2-ethoxy-2-oxoethyl)nicotinic acid

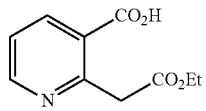

To a solution of sodium ethoxide (29.6 mL, 79.0 mmol) in EtOH (32 mL) was added ethylacetoacetate (6.20 g, 47.6 mmol) dropwise at 0° C. After being stirred for 5 min., 2-chloronicotinic acid (5.00 g, 31.7 mmol) and copper(II) acetate (288 mg, 1.59 mmol) was added thereto. The reaction mixture was stirred at 80° C. for 2 h. After being cooled to room temperature, the mixture was acidified with AcOH. The mixture was concentrated in vacuo. The residue was extracted with DCM and water. The separated organic layer was dried over Na$_2$SO$_4$, filtered and concentrated in vacuo. The residue was triturated with hexanes and collected by filtration to give 2-(2-ethoxy-2-oxoethyl)nicotinic acid (3.98 g, 60%) as a yellow solid. $^1$H-NMR (CDCl$_3$, Varian, 400 MHz): δ 1.26 (3H, t, J=7.2 Hz), 4.19 (2H, q, J=7.2 Hz), 4.38 (2H, s), 7.43 (1H, s), 8.47 (1H, d, J=7.2 Hz), 8.79 (1H, s).

Step B: ethyl 2-(2-ethoxy-2-oxoethyl)nicotinate

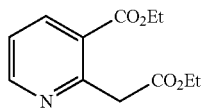

A mixture of 2-(2-ethoxy-2-oxoethyl)nicotinic acid (1.00 g, 4.78 mmol) and NaHCO$_3$ (446 mg, 5.31 mmol) in DMF (5.3 mL) was added ethyl iodide (579 μL, 7.17 mmol) at room temperature. The reaction mixture was stirred 80° C. for 3 h. The mixture was partitioned between water and EtOAc. The separated organic layer was washed with water and brine, dried over Na$_2$SO$_4$, filtered and concentrated in vacuo. The residue was purified by column chromatography on SiO$_2$ (Hex:EtOAc=1:4 to 1:2) to give ethyl 2-(2-ethoxy-2-oxoethyl)nicotinate (1.13 g, 83%) as a yellow oil. $^1$H-NMR (CDCl$_3$, Varian, 400 MHz): δ 1.26 (3H, t, J=7.2 Hz), 1.39 (3H, t, J=7.2 Hz), 4.18 (2H, q, J=7.2 Hz), 4.29 (2H, s), 4.37 (2H, q, J=7.2 Hz), 7.33 (1H, dd, J=8.0, 14.8 Hz), 8.31 (1H, dd, J=8.0, 1.6 Hz), 8.68 (1H, dd, J=4.8, 1.6 Hz).

Step C: ethyl 7-(2-fluoro-4-iodophenylamino)-6-methyl-5-oxo-5,6-dihydro-1,6-naphthyridine-8-carboxylate

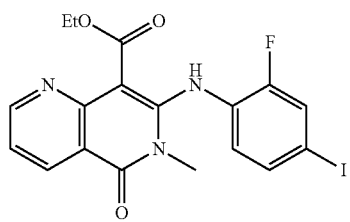 [SMILES: CCOC(=O)c1c(Nc2ccc(I)cc2F)n(C)c(=O)c2cccnc12]

To a solution of ethyl 2-(2-ethoxy-2-oxoethyl)nicotinate (500 mg, 2.11 mmol) in dry THF (7.0 mL) was added NaH (55 wt % dispersion in mineral oil, 101 mg, 2.32 mmol) at 0° C. The reaction mixture was stirred at room temperature for 1 h, and then 2-fluoro-4-iodo-N-((methylimino)methylene)aniline (intermediate 1, 599 mg, 2.17 mmol) in dry THF (3.5 mL) was slowly added thereto at room temperature. The reaction mixture was stirred at room temperature for 4 h. The reaction mixture was quenched with water and extracted with EtOAc. The organic layers were washed with brine, dried over Na$_2$SO$_4$, filtered and concentrated in vacuo. The residue was purified by column chromatography on SiO$_2$ (Hex:EtOAc=4:1 to 1:1) to give ethyl 7-(2-fluoro-4-iodophenylamino)-6-methyl-5-oxo-5,6-dihydro-1,6-naphthyridine-8-carboxylate (800 mg, 81%) as a yellow solid. $^1$H-NMR (CDCl$_3$, Varian, 400 MHz): δ 1.32 (3H, t, J=7.2 Hz), 3.45 (3H, s), 4.40 (2H, q, J=7.2 Hz), 6.42 (1H, t, J=8.4 Hz), 7.35 (1H, d, J=8.4 Hz), 7.38 (1H, dd, J=8.0, 4.8 Hz), 7.48 (1H, dd, J=10.4, 2.0 Hz), 7.93 (1H, s), 8.63 (1H, dd, J=8.0, 2.0 Hz), 8.80 (1H, dd, J=4.4, 2.0 Hz).

Step D: N-(2-(tert-butyldimethylsilyloxy)ethoxy)-7-(2-fluoro-4-iodophenylamino)-6-methyl-5-oxo-5,6-dihydro-1,6-naphthyridine-8-carboxamide

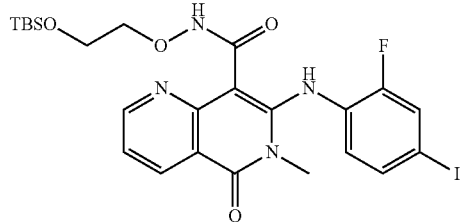 [SMILES: Cn1c(Nc2ccc(I)cc2F)c(C(=O)NOCCO[Si](C)(C)C(C)(C)C)c2ncccc2c1=O]

A mixture of ethyl 7-(2-fluoro-4-iodophenylamino)-6-methyl-5-oxo-5,6-dihydro-1,6-naphthyridine-8-carboxylate (100 mg, 0.214 mmol) and O-(2-(tert-butyldimethylsilyloxy)ethyl)hydroxylamine (intermediate 2, 819 mg, 4.28 mmol) was stirred at 150° C. with microwave irradiation for 2 h. After being cooled to room temperature, the reaction mixture was purified by column chromatography on SiO$_2$ (Hex:EtOAc=4:1) to give N-(2-(tert-butyldimethylsilyloxy)ethoxy)-7-(2-fluoro-4-iodophenylamino)-6-methyl-5-oxo-5,6-dihydro-1,6-naphthyridine-8-carboxamide (29.0 mg, 22%) as a yellow oil. $^1$H-NMR (CDCl$_3$, Varian, 400 MHz): δ 0.07 (6H, s), 0.89 (9H, s), 3.32 (3H, s), 3.91 (2H, t, J=4.8 Hz), 4.12 (2H, t, J=4.8 Hz), 6.60 (1H, t, J=8.4 Hz), 7.26-7.33 (1H, m), 7.38 (1H, d, J=8.4 Hz), 7.47 (1H, d, J=11.2 Hz), 8.69 (1H, d, J=8.0 Hz), 8.79 (1H, dd, J=4.6, 2.0 Hz), 12.46 (1H, s), 13.75 (1H, s).

Step E: 7-(2-fluoro-4-iodophenylamino)-N-(2-hydroxyethoxy)-6-methyl-5-oxo-5,6-dihydro-1,6-naphthyridine-8-carboxamide

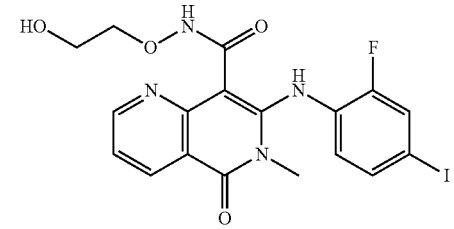 [SMILES: Cn1c(Nc2ccc(I)cc2F)c(C(=O)NOCCO)c2ncccc2c1=O]

To a solution of ethyl N-(2-(tert-butyldimethylsilyloxy)ethoxy)-7-(2-fluoro-4-iodophenylamino)-6-methyl-5-oxo-5,6-dihydro-1,6-naphthyridine-8-carboxamide (29.0 mg, 0.047 mmol) in THF (1.0 mL) was added TBAF (1.0 M solution in THF, 4.73 mL, 4.73 mmol) at room temperature. The reaction mixture was stirred for 4 h at room temperature, and then partitioned between EtOAc and water. The separated organic layer was washed with brine, dried over Na$_2$SO$_4$, filtered and concentrated in vacuo. The residue was purified by column chromatography on SiO$_2$ (Hex:EtOAc=1:9) to give ethyl 7-(2-fluoro-4-iodophenylamino)-N-(2-hydroxyethoxy)-6-methyl-5-oxo-5,6-dihydro-1,6-naphthyridine-8-carboxamide (21.5 mg, 91%) as a yellow solid. MS m/z=498.9 [M+1]$^+$ detected; $^1$HNMR (CDCl$_3$, Varian, 400 MHz): δ 3.30 (3H, s), 3.72-3.76 (2H, m), 4.09 (2H, t, J=4.8 Hz), 4.43 (1H, t, J=5.2 Hz), 6.64 (1H, t, J=8.4 Hz), 7.24-7.34 (1H, m), 7.40 (1H, d, J=8.4 Hz), 7.48 (1H, dd, J=9.6, 2.0 Hz), 8.67 (1H, dd, J=8.0, 2.0 Hz), 8.79 (1H, dd, J=4.8, 2.0 Hz), 12.21 (1H, s), 13.91 (1H, s).

Example 2

8-(5-amino-1,3,4-oxadiazol-2-yl)-7-(2-fluoro-4-iodophenylamino)-6-methyl-1,6-naphthyridin-5(6H)-one

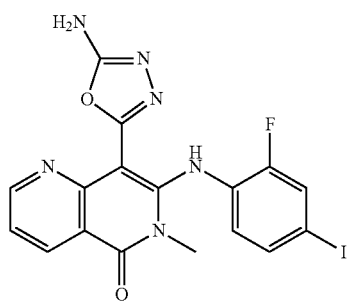 [SMILES: Cn1c(Nc2ccc(I)cc2F)c(-c2nnc(N)o2)c2ncccc2c1=O]

A mixture of ethyl 7-(2-fluoro-4-iodophenyl amino)-6-methyl-5-oxo-5,6-dihydro-1,6-naphthyridine-8-carboxylate (50.0 mmg, 0.107 mmol; prepared as in Example 1, Step C) and hydrazine monohydrate (26.0 µL, 0.535 mmol) in EtOH (1.0 mL) was stirred at 90° C. overnight. After being cooled to room temperature, the mixture was concentrated in vacuo to give the carbohydrazide (48.0 mg, quant.) as a yellow solid, which was used for the next step without further purification. To a mixture of carbohydrazide (48.0 mg, 0.107 mmol) and added cyanic bromide (14.0 mg, 0.128 mmol) in dioxane (1.0 mL) was added 1N NaHCO$_3$ (64.0 µL, 0.064 mmol) at room temperature. After being stirred for 1 h at room temperature, the mixture was partitioned between water and extracted with EtOAc. The organic layers were washed with brine, dried over Na$_2$SO$_4$, filtered and concentrated in vacuo. The residue was purified by column chromatography on SiO$_2$ (DCM (saturated with NH$_3$): MeOH=97:3) to give 8-(5-amino-1,3,4-oxadiazol-2-yl)-7-(2-fluoro-4-iodophenylamino)-6-methyl-1,6-naphthyridin-5 (6H)-one (5.0 mg, 10%) as a yellow solid. MS m/z=479.1 [M+1]$^+$ detected; $^1$H-NMR (CDCl$_3$, Varian, 400 MHz): δ 3.45 (3H, s), 5.10 (2H, brs), 6.45 (1H, t, J=4.8 Hz), 7.34 (1H, d, J=8.4 Hz), 7.37-7.40 (1H, m), 7.46 (1H, dd, J=10.0, 2.0 Hz), 8.67 (1H, dd, J=8.0, 2.0 Hz), 8.90 (1H, dd, J=4.4, 2.0 Hz), 9.24 (1H, s).

Example 3

3-(2-fluoro-4-iodophenylamino)-N-(2-hydroxyethoxy)-2-methyl-1-oxo-2,5,6,7-tetrahydro-1H-cyclopenta[c]pyridine-4-carboxamide

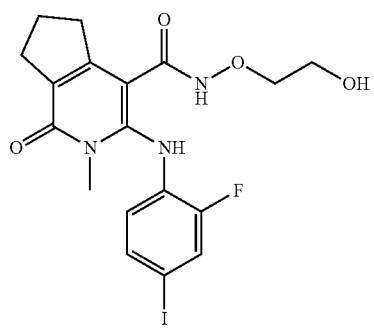 [SMILES: Cn1c(Nc2ccc(I)cc2F)c(C(=O)NOCCO)c2c(c1=O)CCC2]

Step A: Ethyl 2-(2-ethoxy-2-oxoethyl)cyclopent-1-enecarboxylate

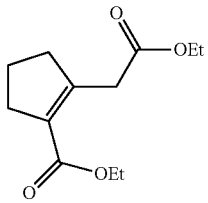 [SMILES: CCOC(=O)CC1=C(C(=O)OCC)CCC1]

A mixture of ethyl 2-oxocyclopentanecarboxylate (5.00 g, 32.0 mmol) and tributyl(2-ethoxy-2-oxoethyl)phosphonium bromide (17.7 g, 48.0 mmol) in toluene (5.34 mL) was stirred at 120° C. for 18 hours. After being concentrated in vacuo, the residue was purified by flash column chromatography on SiO$_2$ (Hex:EtOAc=5:1) to give ethyl 2-(2-ethoxy-2-oxoethyl)cyclopent-1-enecarboxylate (2.61 g, 36%) as a colorless oil. $^1$H NMR (CDCl$_3$, Varian 400 MHz): δ 1.23-1.30 (6H, m), 1.84-1.91 (2H, m), 2.56-2.61 (2H, m), 2.65-2.68 (2H, m), 3.68 (2H, s), 4.12-4.21 (4H, m).

Step B: Ethyl 3-(2-fluoro-4-iodophenylamino)-2-methyl-1-oxo-2,5,6,7-tetrahydro-1H-cyclopenta[c]pyridine-4-carboxylate

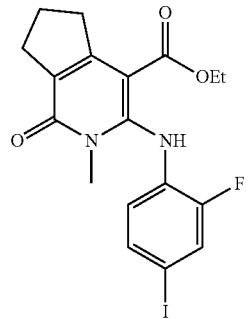 [SMILES: CCOC(=O)c1c2c(c(=O)n(C)c1Nc1ccc(I)cc1F)CCC2]

To a solution of ethyl 2-(2-ethoxy-2-oxoethyl)cyclopent-1-enecarboxylate (500 mg, 2.21 mmol) in dry THF (70 mL) was added NaH (55%, 1.06 g, 24.3 mmol) at 0° C. After being stirred at 0° C. for 1 hour, a solution of 2-fluoro-4-iodo-N-((methylimino)methylene)aniline (intermediate 1, 671 mg, 2.43 mmol) in THF (40 mL) was added thereto at 0° C. The reaction mixture was stirred at room temperature for 2 hours, quenched with saturated aq. NH$_4$Cl and extracted with EtOAc. The residue was purified by flash column chromatography on SiO$_2$ (EtOAc), and then recrystallized from EtOAc and diethyl ether to give ethyl 3-(2-fluoro-4-iodophenylamino)-2-methyl-1-oxo-2,5,6,7-tetrahydro-1H-cyclopenta[c]pyridine-4-carboxylate (200 mg, 20%) as a white solid. $^1$H NMR (CDCl$_3$, Varian 400 MHz): δ 1.36 (3H, t, J=7.2 Hz), 2.05 (2H, p, J=7.6 Hz), 2.84 (2H, t, J=7.6 Hz), 3.20 (2H, t, J=7.6 Hz), 3.31 (3H, s), 4.29 (2H, q, J=7.2 Hz), 6.36-6.41 (1H, m), 7.32-7.35 (1H, m), 7.47 (1H, dd, J=10.0, 2.0 Hz), 9.77 (1H, brs).

Step C: N-(2-(tert-butyldimethylsilyloxy)ethoxy)-3-(2-fluoro-4-iodophenylamino)-2-methyl-1-oxo-2,5,6,7-tetrahydro-1H-cyclopenta[c]pyridine-4-carboxamide

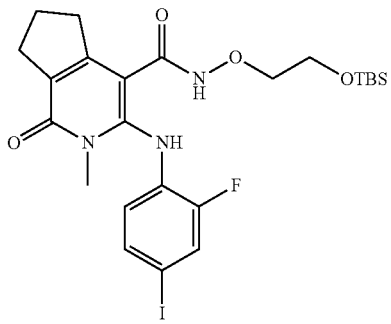 [SMILES: Cn1c(Nc2ccc(I)cc2F)c(C(=O)NOCCO[Si](C)(C)C(C)(C)C)c2c(c1=O)CCC2]

To a mixture of ethyl 3-(2-fluoro-4-iodophenylamino)-2-methyl-1-oxo-2,5,6,7-tetrahydro-1H-cyclopenta[c]pyridine-4-carboxylate (683 mg, 1.50 mmol) and O-(2-(tert-butyldimethylsilyloxy)ethyl)hydroxylamine (intermediate 2, 430 mg, 2.25 mmol) in THF (5 mL) was added LiHMDS (1.0 M in THF/ethylbenzene, 11.98 mL, 11.98 mmol) at 0° C. After being stirred for 3 hours at room temperature, the mixture was quenched with saturated aq. NH$_4$Cl, extracted with EtOAc. The organic layer was washed water and brine, dried over Na$_2$SO$_4$, filtered and concentrated in vacuo. The residue was purified by column chromatography on SiO$_2$ (Hex:EtOAc=1:3) to give N-(2-(tert-butyldimethylsilyloxy)ethoxy)-3-(2-fluoro-4-iodophenylamino)-2-methyl-1-oxo-2,5,6,7-tetrahydro-1H-cyclopenta[c]pyridine-4-carboxamide (700 mg, 78%) as a white solid. $^1$H-NMR (CDCl$_3$, Varian, 400 MHz): δ 0.01 (6H, s), 0.86 (9H, s), 2.09 (2H, p, J=7.6 Hz), 2.85 (2H, t, J=7.6 Hz), 3.02 (2H, t, J=7.4 Hz), 3.35 (3H, s), 3.86-3.88 (2H, m), 3.97-3.40 (2H, m), 6.29 (1H, t, J=8.6 Hz), 7.28-7.31 (1H, m), 7.43 (1H, dd, J=10.0, 2.0 Hz), 8.80 (1H, brs), 8.91 (1H, brs).

Step D: 3-(2-fluoro-4-iodophenylamino)-N-(2-hydroxyethoxy)-2-methyl-1-oxo-2,5,6,7-tetrahydro-1H-cyclopenta[c]pyridine-4-carboxamide

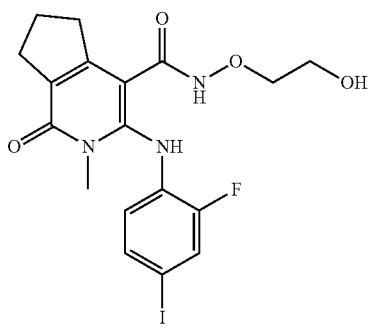 [SMILES: Cn1c(Nc2ccc(I)cc2F)c(C(=O)NOCCO)c2c(c1=O)CCC2]

To a solution of N-(2-(tert-butyldimethylsilyloxy)ethoxy)-3-(2-fluoro-4-iodophenylamino)-2-methyl-1-oxo-2,5,6,7-tetrahydro-1H-cyclopenta[c]pyridine-4-carboxamide (400 mg, 0.665 mmol) in THF (2 mL) was added TBAF (1.0 M in THF, 6.65 mL, 6.65 mmol) at room temperature. After being stirred for 2 hours at room temperature, the mixture was partitioned between EtOAc and water. The separated organic layer was washed with water and brine, dried over anhydrous Na$_2$SO$_4$, filtered and concentrated in vacuo. The residue was recrystallized from EtOAc and DCM to give 3-(2-fluoro-4-iodophenylamino)-N-(2-hydroxyethoxy)-2-methyl-1-oxo-2,5,6,7-tetrahydro-1H-cyclopenta[c]pyridine-4-carboxamide (264 mg, 81%) as a white solid. MS m/z=488.0 [M+1]$^+$ detected; $^1$H-NMR (MeOD, Varian, 400 MHz): δ 2.08 (2H, p, J=7.6 Hz), 2.79 (2H, t, J=7.6 Hz), 2.92 (2H, t, J=7.6 Hz), 3.48 (3H, s), 3.55-3.57 (2H, m), 3.66-3.68 (2H, m), 6.48 (1H, t, J=8.6 Hz), 7.32-7.35 (1H, m), 7.45 (1H, dd, J=10.8, 2.0 Hz).

Example 4

3-(2-fluoro-4-iodophenylamino)-2-methyl-1-oxo-2,5,6,7-tetrahydro-1H-cyclopenta[c]pyridine-4-carboxamide

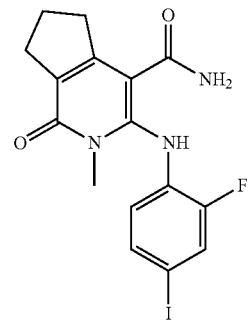 [SMILES: Cn1c(Nc2ccc(I)cc2F)c(C(N)=O)c2c(c1=O)CCC2]

To a solution of ethyl 3-(2-fluoro-4-iodophenylamino)-2-methyl-1-oxo-2,5,6,7-tetrahydro-1H-cyclopenta[c]pyridine-4-carboxylate (150 mg, 0.329 mmol; prepared as in Example 3, Step B) in MeOH (1 mL) was added 1 N aq. NaOH (3.29 mL, 3.29 mmol) at room temperature. After being stirred for 1 day at room temperature, the reaction mixture was neutralized with 1 N aq. HCl solution, while a white solid was precipitated. The solid was collected by filtration and rinsed with water (50 mL) to give 3-(2-fluoro-4-iodophenylamino)-2-methyl-1-oxo-2,5,6,7-tetrahydro-1H-cyclopenta[c]pyridine-4-carboxylic acid (133 mg, 94%) as a white solid. A mixture of 3-(2-fluoro-4-iodophenylamino)-2-methyl-1-oxo-2,5,6,7-tetrahydro-1H-cyclopenta[c]pyridine-4-carboxylic acid (50 mg, 0.117 mmol), NH4Cl (12.49 mg, 0.234 mmol), EDCI (26.9 mg, 0.140 mmol), HOBT (21.5 mg, 0.140 mmol) and DIPEA (61.2 μL, 0.350 mmol) in DMF (500 μL) was stirred for 17 hours at room temperature. The reaction mixture was diluted with water, while a white solid was precipitated. The solid was collected by filtration, rinsed with water and EtOAc, and then dried under reduced pressure to give 3-(2-fluoro-4-iodophenylamino)-2-methyl-1-oxo-2,5,6,7-tetrahydro-1H-cyclopenta[c]pyridine-4-carboxamide (22 mg, 44%) as a white solid. MS m/z=428.1 [M+1]$^+$ detected; $^1$H-NMR (MeOD, Varian, 400 MHz): δ 2.09 (2H, p, J=8.0 Hz), 2.81 (2H, t, J=7.6 Hz), 3.01 (2H, t, J=7.6 Hz), 3.45 (3H, s), 6.44 (1H, t, J=8.6 Hz), 7.32-7.35 (1H, m), 7.46 (1H, dd, J=10.4, 2.0 Hz).

Example 5

(S)-3-(2-fluoro-4-iodophenylamino)-N-(2-hydroxypropoxy)-2-methyl-1-oxo-2,5,6,7-tetrahydro-1H-cyclopenta[c]pyridine-4-carboxamide

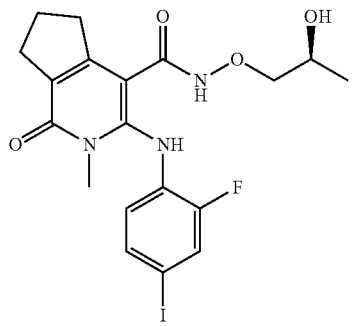 [SMILES: C[C@H](O)CONC(=O)c1c2c(c(=O)n(C)c1Nc1ccc(I)cc1F)CCC2]

Step A: (S)—N-(2-(tert-butyldimethylsilyloxy)propoxy)-3-(2-fluoro-4-iodophenylamino)-2-methyl-1-oxo-2,5,6,7-tetrahydro-1H-cyclopenta[c]pyridine-4-carboxamide

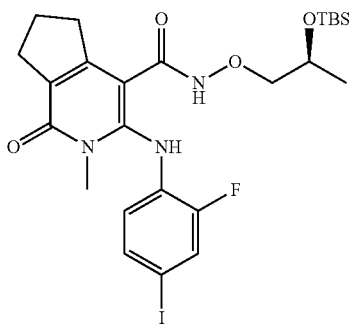 [SMILES: C[C@@H](CONC(=O)c1c2c(c(=O)n(C)c1Nc1ccc(I)cc1F)CCC2)O[Si](C)(C)C(C)(C)C]

To a mixture of ethyl 3-(2-fluoro-4-iodophenylamino)-2-methyl-1-oxo-2,5,6,7-tetrahydro-1H-cyclopenta[c]pyridine-4-carboxylate (100 mg, 0.219 mmol; prepared as in Example 3, Step B) and (S)—O-(2-(tert-butyldimethylsilyloxy)propyl)hydroxylamine (intermediate 3, 67.5 mg, 0.329 mmol) in THF (0.7 mL) was added LiHMDS (1.0 M in THF/ethylbenzene, 1.75 mL, 1.75 mmol) at 0° C. After being stirred for overnight at room temperature, the mixture was quenched with saturated aq. NH₄Cl, extracted with EtOAc. The organic layer was washed water and brine, dried over Na₂SO₄, filtered and concentrated in vacuo. The residue was purified by column chromatography on SiO₂ (Hex:EtOAc=1:2) to give (S)—N-(2-(tert-butyldimethylsilyloxy)propoxy)-3-(2-fluoro-4-iodophenylamino)-2-methyl-1-oxo-2,5,6,7-tetrahydro-1H-cyclopenta[c]pyridine-4-carboxamide (78 mg, 58%) as a yellow solid. $^1$H-NMR (CDCl₃, Varian, 400 MHz): δ 0.02 (3H, s), 0.06 (3H, s), 0.85 (9H, s), 1.16 (3H, d, J=6.4 Hz), 2.08-2.11 (2H, m), 2.84 (2H, t, J=7.4 Hz), 3.02 (2H, t, J=7.2 Hz), 3.35 (3H, s), 3.71-3.75 (1H, m), 3.82-3.86 (1H, m), 4.04-4.09 (1H, m), 6.28 (1H, t, J=8.6 Hz), 7.28-7.31 (1H, m), 7.43 (1H, dd, J=10.0, 2.0 Hz), 8.65 (1H, brs), 8.92 (1H, brs).

Step B: (S)-3-(2-fluoro-4-iodophenylamino)-N-(2-hydroxypropoxy)-2-methyl-1-oxo-2,5,6,7-tetrahydro-1H-cyclopenta[c]pyridine-4-carboxamide

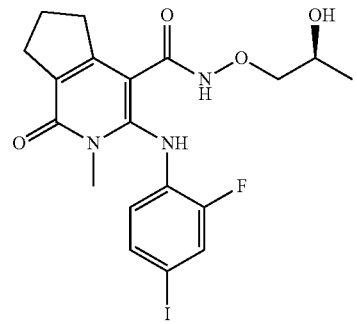 [SMILES: C[C@H](O)CONC(=O)c1c2c(c(=O)n(C)c1Nc1ccc(I)cc1F)CCC2]

To a solution of (S)—N-(2-(tert-butyldimethylsilyloxy)propoxy)-3-(2-fluoro-4-iodophenylamino)-2-methyl-1-oxo-2,5,6,7-tetrahydro-1H-cyclopenta[c]pyridine-4-carboxamide (78.0 mg, 0.127 mmol) in THF (0.4 mL) was added TBAF (1.0 M in THF, 1.267 mL, 1.267 mmol) at room temperature. After being stirred for 3 hours at room temperature, the mixture was partitioned between EtOAc and water. The separated organic layer was washed with water and brine, dried over anhydrous Na₂SO₄, filtered and concentrated in vacuo. The residue was purified by column chromatography on SiO₂ (EtOAc) to give (S)-3-(2-fluoro-4-iodophenylamino)-N-(2-hydroxypropoxy)-2-methyl-1-oxo-2,5,6,7-tetrahydro-1H-cyclopenta[c]pyridine-4-carboxamide (12 mg, 19%) as a yellow solid. MS m/z=502.0 [M+1]⁺ detected; $^1$H-NMR (CDCl₃, Varian, 400 MHz): δ 1.13 (3H, d, J=6.4 Hz), 2.10-2.14 (2H, m), 2.56 (2H, t, J=7.6 Hz), 3.02 (2H, t, J=7.4 Hz), 3.34 (3H, s), 3.62-3.67 (1H, m), 3.85-3.88 (1H, m), 3.93-3.97 (1H, m), 6.34 (1H, t, J=8.4 Hz), 7.33 (1H, d, J=8.0 Hz), 7.45 (1H, dd, J=10.0, 1.6 Hz), 8.47 (1H, brs), 8.86 (1H, brs).

Example 6

(R)-3-(2-fluoro-4-iodophenylamino)-N-(2-hydroxypropoxy)-2-methyl-1-oxo-2,5,6,7-tetrahydro-1H-cyclopenta[c]pyridine-4-carboxamide

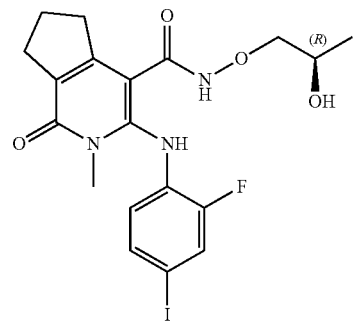

Step A: (R)—N-(2-(tert-butyldimethylsilyloxy)
propoxy)-3-(2-fluoro-4-iodophenylamino)-2-methyl-
1-oxo-2,5,6,7-tetrahydro-1H-cyclopenta[c]pyridine-
4-carboxamide

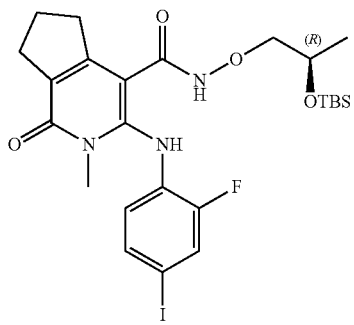

To a mixture of ethyl 3-(2-fluoro-4-iodophenylamino)-2-methyl-1-oxo-2,5,6,7-tetrahydro-1H-cyclopenta[c]pyridine-4-carboxylate (150 mg, 0.329 mmol; prepared as in Example 3, Step B) and (R)—O-(2-(tert-butyldimethylsilyloxy)propyl)hydroxylamine (intermediate 4, 101 mg, 0.493 mmol) in THF (2 mL) was added LiHMDS (1.0 M in THF/ethylbenzene, 2.63 mL, 2.63 mmol) at 0° C. After being stirred at room temperature for 5 hours, the reaction mixture was quenched with saturated aq.NH$_4$Cl, extracted with EtOAc. The organic layer was washed water and brine, dried over Na$_2$SO$_4$, filtered and concentrated in vacuo. The residue was purified by column chromatography on SiO$_2$ (Hex: EtOAc=1:2) to give (R)—N-(2-(tert-butyldimethylsilyloxy)propoxy)-3-(2-fluoro-4-iodophenylamino)-2-methyl-1-oxo-2,5,6,7-tetrahydro-1H-cyclopenta[c]pyridine-4-carboxamide (194 mg, 96% yield) as a yellow solid. $^1$H-NMR (CDCl$_3$, Varian, 400 MHz): δ 0.02 (3H, s), 0.06 (3H, s), 0.84 (9H, s), 1.17 (3H, d, J=6.0 Hz), 2.07-2.10 (2H, m), 2.85 (2H, t, J=7.6 Hz), 3.00-3.02 (2H, m), 3.36 (3H, s), 3.75 (1H, m), 3.84-3.87 (1H, m), 4.04-4.08 (1H, m), 6.28 (1H, t, J=8.6 Hz), 7.28-7.31 (1H, m), 7.44 (1H, dd, J=10.2, 2.1 Hz), 8.70 (1H, brs), 8.80 (1H, brs).

Step B: (R)-3-(2-fluoro-4-iodophenylamino)-N-(2-
hydroxypropoxy)-2-methyl-1-oxo-2,5,6,7-tetra-
hydro-1H-cyclopenta[c]pyridine-4-carboxamide

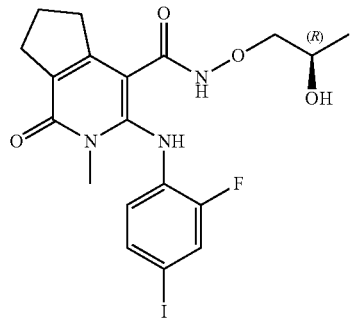

To a solution of (R)—N-(2-(tert-butyldimethylsilyloxy)propoxy)-3-(2-fluoro-4-iodophenylamino)-2-methyl-1-oxo-2,5,6,7-tetrahydro-1H-cyclopenta[c]pyridine-4-carboxamide (194 mg, 0.315 mmol) in THF (2 mL) was added TBAF (1.0 M in THF, 3.15 mL, 3.15 mmol) at room temperature. After being stirred at room temperature for 17 hours, the mixture was partitioned between EtOAc and water. The separated organic layer was washed with water and brine, dried over anhydrous Na$_2$SO$_4$, filtered and concentrated in vacuo. The residue was purified by column chromatography on SiO$_2$ (EtOAc) to give (R)-3-(2-fluoro-4-iodophenylamino)-N-(2-hydroxypropoxy)-2-methyl-1-oxo-2,5,6,7-tetrahydro-1H-cyclopenta[c]pyridine-4-carboxamide (40 mg, 25% yield) as a yellow solid. MS m/z=502.0 [M+1]$^+$ detected; $^1$H-NMR (CDCl$_3$, Varian, 400 MHz): δ 1.13 (3H, d, J=6.4 Hz), 2.10-2.14 (2H, m), 2.86 (2H, t, J=7.6 Hz), 3.02 (2H, t, J=7.4 Hz), 3.34 (3H, s), 3.65 (1H, dd, J=11.4, 9.4 Hz), 3.86 (1H, dd, J=11.2, 2.0 Hz), 3.93-3.97 (1H, m), 6.34 (1H, t, J=8.6 Hz), 7.33 (1H, d, J=8.4 Hz), 7.45 (1H, dd, J=10.0, 1.6 Hz), 8.46 (1H, brs), 8.86 (1H, brs). *One protone from OH was not observed.

Example 7

3-(2-fluoro-4-iodophenylamino)-N-(2-hydroxy-2-
methylpropoxy)-2-methyl-1-oxo-2,5,6,7-tetrahydro-
1H-cyclopenta[c]pyridine-4-carboxamide

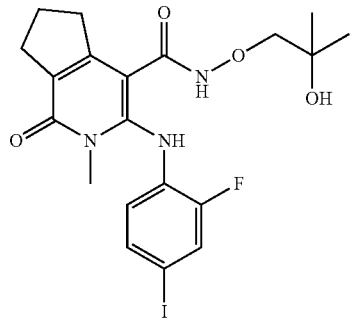 [SMILES: Cn1c(Nc2ccc(I)cc2F)c(C(=O)NOCC(C)(C)O)c2c(c1=O)CCC2]

Step A: N-(2-(tert-butyldimethylsilyloxy)-2-methyl-
propoxy)-3-(2-fluoro-4-iodophenylamino)-2-methyl-
1-oxo-2,5,6,7-tetrahydro-1H-cyclopenta[c]pyridine-
4-carboxamide

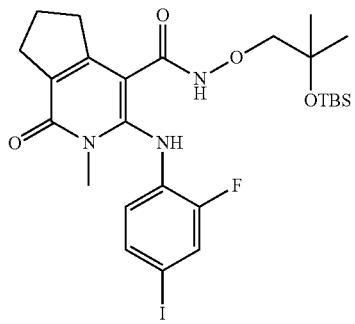 [SMILES: Cn1c(Nc2ccc(I)cc2F)c(C(=O)NOCC(C)(C)O[Si](C)(C)C(C)(C)C)c2c(c1=O)CCC2]

To a mixture of ethyl 3-(2-fluoro-4-iodophenylamino)-2-methyl-1-oxo-2,5,6,7-tetrahydro-1H-cyclopenta[c]pyridine-4-carboxylate (222 mg, 0.487 mmol; prepared as in Example 3, Step B) and O-(2-(tert-butyldimethylsilyloxy)-2-methylpropyl)hydroxylamine (intermediate 5, 160 mg, 0.730 mmol) in THF (2.5 mL) was added LiHMDS (1.0 M in THF/ethylbenzene, 3.89 mL, 3.89 mmol) at 0° C. After being stirred at room temperature for 5 hours, the reaction mixture was quenched with saturated aq. NH₄Cl, extracted with EtOAc. The organic layer was washed water and brine, dried over Na₂SO₄, filtered and concentrated in vacuo. The residue was purified by column chromatography on SiO₂ (Hex:EtOAc=1:2) to give N-(2-(tert-butyldimethylsilyloxy)-2-methylpropoxy)-3-(2-fluoro-4-iodophenylamino)-2-meth yl-1-oxo-2,5,6,7-tetrahydro-1H-cyclopenta[c]pyridine-4-carboxamide (217 mg, 71%) as a yellow solid. (CDCl₃, Varian, 400 MHz): δ 0.07 (3H, s), 0.79 (9H, s), 1.26 (6H, s), 2.04-2.12 (2H, m), 2.83 (2H, t, J=7.4 Hz), 3.01 (2H, t, J=7.6 Hz), 3.35 (3H, s), 3.64 (2H, s), 6.27 (1H, t, J=8.6 Hz), 7.28-7.31 (1H, m), 7.43 (1H, dd, J=10.0, 2.0 Hz), 8.37 (1H, brs), 8.98 (1H, brs).

Step B: 3-(2-fluoro-4-iodophenylamino)-N-(2-hydroxy-2-methylpropoxy)-2-methyl-1-oxo-2,5,6,7-tetrahydro-1H-cyclopenta[c]pyridine-4-carboxamide

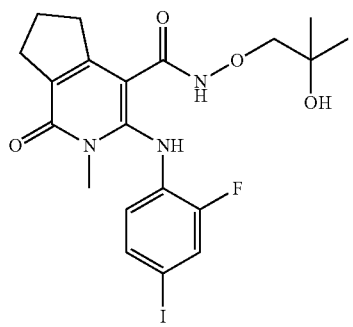 [SMILES: Cn1c(Nc2ccc(I)cc2F)c(C(=O)NOCC(C)(C)O)c2c(c1=O)CCC2]

To a solution of N-(2-(tert-butyldimethylsilyloxy)-2-methylpropoxy)-3-(2-fluoro-4-iodophenylamino)-2-methyl-1-oxo-2,5,6,7-tetrahydro-1H-cyclopenta[c]pyridine-4-carboxamide (210 mg, 0.334 mmol) in THF (2 mL) was added TBAF (1.0 M in THF, 3.34 mL, 3.34 mmol) at room temperature. After being stirred at room temperature for 17 hours, the mixture was partitioned between EtOAc and water. The separated organic layer was washed with water and brine, dried over anhydrous Na₂SO₄, filtered and concentrated in vacuo. The residue was purified by column chromatography on SiO₂ (EtOAc only) to give 3-(2-fluoro-4-iodophenylamino)-N-(2-hydroxy-2-methylpropoxy)-2-methyl-1-oxo-2,5,6,7-tetrahydro-1H-cyclopenta[c]pyridine-4-carboxamide (12.0 mg, 7%) as a yellow solid. MS m/z=516.0 (M+H)⁺ detected; ¹H-NMR (CD₃OD, Varian, 400 MHz): δ 1.15 (6H, s), 2.04-2.12 (2H, m), 2.79 (2H, t, J=7.6 Hz), 2.92 (2H, t, J=7.4 Hz), 3.39 (2H, s), 3.49 (3H, s), 6.50 (1H, t, J=8.8 Hz), 7.33-7.36 (1H, m), 7.45 (1H, dd, J=10.6, 1.8 Hz). *Three protons from NH, NH, OH were not observed.

Example 8

N-(2,3-dihydroxypropoxy)-3-(2-fluoro-4-iodophenylamino)-2-methyl-1-oxo-2,5,6,7-tetrahydro-1H-cyclopenta[c]pyridine-4-carboxamide

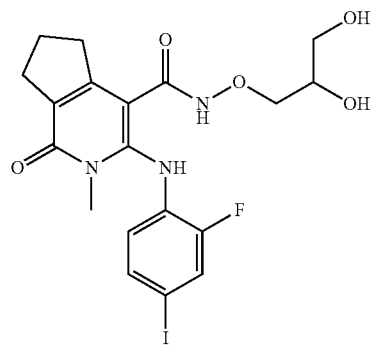 [SMILES: Cn1c(Nc2ccc(I)cc2F)c(C(=O)NOCC(O)CO)c2c(c1=O)CCC2]

Step A: 3-(2-fluoro-4-iodophenylamino)-2-methyl-1-oxo-2,5,6,7-tetrahydro-1H-cyclopenta[c]pyridine-4-carboxylic acid

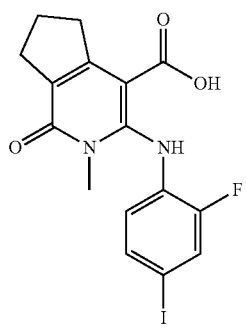

To a solution of ethyl 3-(2-fluoro-4-iodophenylamino)-2-methyl-1-oxo-2,5,6,7-tetrahydro-1H-cyclopenta[c]pyridine-4-carboxylate (758 mg, 1.66 mmol; prepared as in Example 3, Step B) in MeOH (17 mL) was added a solution of LiOH (199 mg, 8.31 mmol) in water (17 mL). The reaction mixture was stirred at 50° C. for 4 hours. After being cooled to room temperature, the mixture was quenched with 2 N aq. HCl and extracted with EtOAc. The separated organic layer was washed with brine, dried over Na₂SO₄, filtered and concentrated in vacuo. The residue was triturated with EtOAc. The precipitate was collected by filtration and rinsed with hexanes to give the 3-(2-fluoro-4-iodophenylamino)-2-methyl-1-oxo-2,5,6,7-tetrahydro-1H-cyclopenta[c]pyridine-4-carboxylic acid (460 mg, 65%) as a yellow solid.

¹H-NMR (DMSO-d₆, Varian, 400 MHz): δ 1.95 (2H, qi, J=7.2 Hz), 2.66 (2H, t, J=7.2 Hz), 3.09 (2H, t, J=7.2 Hz), 3.20 (3H, s), 6.56 (1H, t, J=8.8 Hz), 7.40 (1H, dd, J=8.4, 1.2 Hz), 7.66 (1H, dd, J=2.0, 10.8 Hz), 9.61 (1H, brs). One proton from NH was not observed.

Step B: N-((2,2-dimethyl-1,3-dioxolan-4-yl)
methoxy)-3-(2-fluoro-4-iodophenylamino)-2-
methyl-1-oxo-2,5,6,7-tetrahydro-1H-cyclopenta[c]
pyridine-4-carboxamide

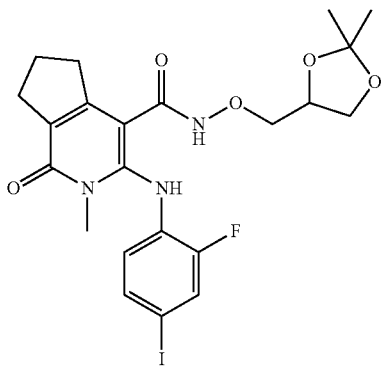 [SMILES: Cn1c(Nc2ccc(I)cc2F)c(C(=O)NOCC2COC(C)(C)O2)c2c(c1=O)CCC2]

To a solution of 3-(2-fluoro-4-iodophenylamino)-2-methyl-1-oxo-2,5,6,7-tetrahydro-1H-cyclopenta[c]pyridine-4-carboxylic acid (200 mg, 0.467 mmol) in DMF (4 mL) was added O-((2,2-dimethyl-1,3-dioxolan-4-yl)methyl)hydroxylamine (76.0 mg, 0.514 mmol), HATU (231 mh, 0.607 mmol) and TEA (0.130 mL, 0.934 mmol) at room temperature. The reaction mixture was stirred at room temperature for 18 hours. The mixture was partitioned between EtOAc and water. The separated organic layer was washed with brine, dried over $Na_2SO_4$, filtered and concentrated in vacuo to give the N-((2,2-dimethyl-1,3-dioxolan-4-yl)methoxy)-3-(2-fluoro-4-iodophenylamino)-2-methyl-1-oxo-2,5,6,7-tetrahydro-1H-cyclopenta[c]pyridine-4-carboxamide, which was used for the next step without further purifications.

Step C: N-(2,3-dihydroxypropoxy)-3-(2-fluoro-4-iodophenylamino)-2-methyl-1-oxo-2,5,6,7-tetrahydro-1H-cyclopenta[c]pyridine-4-carboxamide

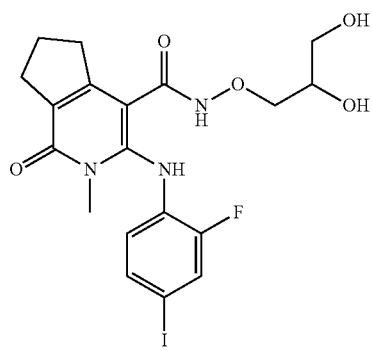 [SMILES: Cn1c(Nc2ccc(I)cc2F)c(C(=O)NOCC(O)CO)c2c(c1=O)CCC2]

To a solution of N-((2,2-dimethyl-1,3-dioxolan-4-yl)methoxy)-3-(2-fluoro-4-iodophenylamino)-2-methyl-1-oxo-2,5,6,7-tetrahydro-1H-cyclopenta[c]pyridine-4-carboxamide (260 mg, 0.467 mmol) in MeOH (5 mL) was added a solution of HCl (1 N in MeOH, 4.67 mL, 4.67 mmol) at 0° C. The reaction mixture was stirred at room temperature for 1 hour. The mixture was diluted with water and extracted with EtOAc. The separated organic layer was dried over $Na_2SO_4$, filtered and concentrated in vacuo. The residue was purified by preparative LC to give the N-(2,3-dihydroxy-propoxy)-3-(2-fluoro-4-iodophenylamino)-2-methyl-1-oxo-2,5,6,7-tetrahydro-1H-cyclopenta[c]pyridine-4-carboxamide (7.00 mg, 3%) as a white solid. $^1$H-NMR (MeOD, Varian, 400 MHz): δ 2.08 (2H, qi, J=7.6 Hz), 2.79 (2H, t, J=8.0 Hz), 2.92 (2H, t, J=7.6 Hz), 3.53-3.45 (5H, m), 3.71-3.56 (3H, m), 6.48 (1H, t, J=8.8 Hz), 7.34 (1H, d, J=8.4 Hz), 7.45 (1H, dd, J=10.8, 2.0 Hz). LC-MS (LC: Agilent LC 1200, MS: LCQ Advantage Max) Mobile phase: from 95% [water+0.01% HBFA+1.0% IPA] and 25% [$CH_3CN$+0.01% HBFA+1.0% IPA] to 5% [water+0.01% HBFA+1.0% IPA] and 95% [$CH_3CN$+0.01% HBFA+1.0% IPA] in 5.0 min) purity is 96.25%, Rt=2.31 min; MS Calcd.: 517.05; MS Found: 518.0 (M+H)$^+$.

Example 9

4-(5-amino-1,3,4-oxadiazol-2-yl)-3-(2-fluoro-4-iodophenylamino)-2-methyl-2,5,6,7-tetrahydro-1H-cyclopenta[c]pyridin-1-one

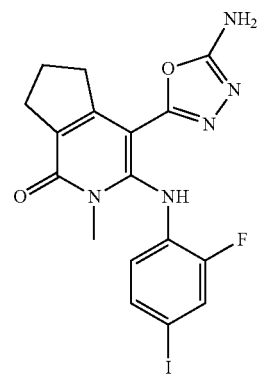 [SMILES: Cn1c(Nc2ccc(I)cc2F)c(-c2nnc(N)o2)c2c(c1=O)CCC2]

Step A: 3-(2-fluoro-4-iodophenylamino)-2-methyl-1-oxo-2,5,6,7-tetrahydro-1H-cyclopenta[c]pyridine-4-carbohydrazide

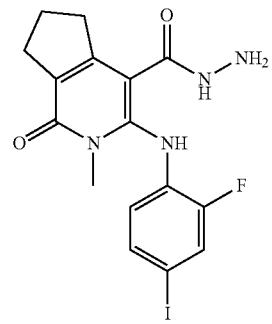 [SMILES: Cn1c(Nc2ccc(I)cc2F)c(C(=O)NN)c2c(c1=O)CCC2]

A mixture of ethyl 3-(2-fluoro-4-iodophenylamino)-2-methyl-1-oxo-2,5,6,7-tetrahydro-1H-cyclopenta[c]pyridine-4-carboxylate (100 mg, 0.219 mmol; prepared as in Example 3, Step B) and hydrazine monohydrate (537 μL, 10.96 mmol) in EtOH (438 μL) was stirred at 90° C. for 17 hours. After cooled to room temperature, the mixture was diluted with water, while a white solid was precipitated. The solid was collected by filtration, washed with water (10 mL) and diethyl ether (3 mL) and then dried under reduced pressure to give the 3-(2-fluoro-4-iodophenylamino)-2-methyl-1-oxo-2,5,6,7-tetrahydro-1H-cyclopenta[c]pyridine-4-carbohydrazide (56.0 mg, 58%) as a white solid. $^1$H-NMR (DMSO-D$_6$, Varian, 400 MHz): δ 1.95-1.98 (2H, m), 2.67 (2H, t, J=7.2 Hz), 2.85 (2H, t, J=7.6 Hz), 3.27 (3H, s), 4.21 (2H, brs), 6.37 (1H, t, J=8.8 Hz), 7.32 (1H, d, J=10.0 Hz), 7.55 (1H, d, J=12.4 Hz), 8.31 (1H, brs), 9.08 (1H, brs).

Step B: 4-(5-amino-1,3,4-oxadiazol-2-yl)-3-(2-fluoro-4-iodophenylamino)-2-methyl-2,5,6,7-tetrahydro-1H-cyclopenta[c]pyridin-1-one

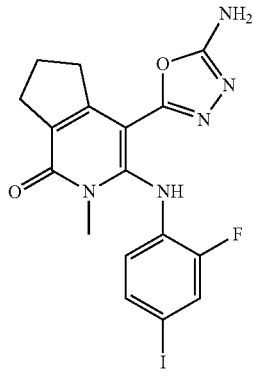 [SMILES: Cn1c(Nc2ccc(I)cc2F)c(-c2nnc(N)o2)c2c(c1=O)CCC2]

To a mixture of 3-(2-fluoro-4-iodophenylamino)-2-methyl-1-oxo-2,5,6,7-tetrahydro-1H-cyclopenta[c]pyridine-4-carbohydrazide (56.0 mg, 0.127 mmol) and cyanic bromide (26.8 mg, 0.253 mmol) in Dioxane (1 mL) was added 1 N aq. NaHCO$_3$ (0.127 mL, 0.127 mmol) at room temperature. After being stirred at room temperature for 1 hour, the reaction mixture was diluted with water and extracted with EtOAc. The organic layer was washed with brine, dried over Na$_2$SO$_4$, filtered and concentrated in vacuo The residue was recrystallized from DCM and MeOH (10:1) to give 4-(5-amino-1,3,4-oxadiazol-2-yl)-3-(2-fluoro-4-iodophenylamino)-2-methyl-2,5,6,7-tetrahydro-1H-cyclopenta[c]pyridin-1-one (22.0 mg, 37%) as a white solid. MS m/z=468.1 [M+1]$^+$ detected; $^1$H-NMR (DMSO-D$_6$, Varian, 400 MHz): δ 1.99-2.04 (2H, m), 2.70-2.74 (2H, m), 2.97-3.01 (2H, m), 3.30 (3H, s), 6.47 (1H, t, J=8.8 Hz), 6.98 (2H, brs), 7.33 (1H, d, J=8.4 Hz), 7.58 (1H, dd, J=11.0, 1.8 Hz), 8.79 (1H, brs).

Example 10

3-(2-fluoro-4-iodophenylamino)-N-(2-hydroxyethoxy)-2,6,6-trimethyl-1-oxo-2,5,6,7-tetrahydro-1H-cyclopenta[c]pyridine-4-carboxamide

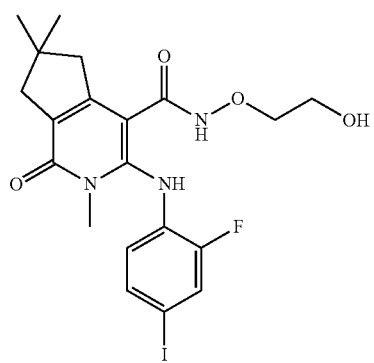 [SMILES: Cn1c(Nc2ccc(I)cc2F)c(C(=O)NOCCO)c2c(c1=O)CC(C)(C)C2]

Step A: 2-Diazo-5,5-dimethylcyclohexane-1,3-dione

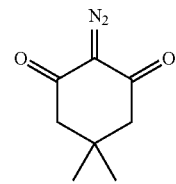

A mixture of 5,5-dimethylcyclohexane-1,3-dione (5.00 g, 35.7 mmol) and 4-acetamidobenzene sulfonyl azide (8.57 g, 35.7 mmol) in ACN (200 mL) was added K$_2$CO$_3$ (9.86 g, 71.3 mmol) at room temperature. The reaction mixture was stirred overnight at room temperature. The mixture was filtered through a silica gel pad and washed with DCM. The filtrated was concentrated in vacuo. The residue was purified by flash column chromatography on SiO$_2$ (Hex:EtOAc=7:3) to give 2-diazo-5,5-dimethylcyclohexane-1,3-dione (5.42 g, 91%) as a yellow solid. $^1$H NMR (CDCl$_3$, Varian 400 MHz): δ 1.12 (6H, s), 2.45 (4H, m).

Step B: Methyl 4,4-dimethyl-2-oxocyclopentanecarboxylate

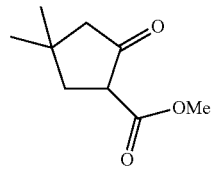

A mixture of 2-diazo-5,5-dimethylcyclohexane-1,3-dione (5.4 g, 32.5 mmol) and MeOH (1.58 mL, 39.0 mmol) in toluene (10 mL) was stirred at 300 W with microwave irradiation for 2 minutes. After being cooled to room temperature, the reaction mixture was purified by column chromatography on SiO$_2$ (Hex:EtOAc=9:1) to give methyl 4,4-dimethyl-2-oxocyclopentanecarboxylate (5.27 g, 95%) as a colorless oil. $^1$H NMR (CDCl$_3$, Varian 400 MHz): δ 1.06 (3H, s), 1.24 (3H, s), 2.19-2.35 (4H, m), 3.39 (1H, dd, J=10.8, 2.2 Hz), 3.74 (3H, s).

Step C: Methyl 2-(2-ethoxy-2-oxoethyl)-4,4-dimethylcyclopent-1-enecarboxylate

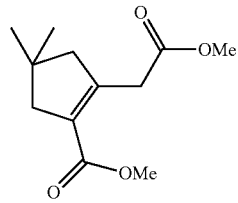 [SMILES: COC(=O)CC1=C(C(=O)OC)CC(C)(C)C1]

A mixture of methyl 4,4-dimethyl-2-oxocyclopentanecarboxylate (5.27 g, 31.0 mmol) and tributyl(2-methoxy-2-oxoethyl)phosphonium bromide (16.5 g, 46.4 mmol) in toluene (5.0 mL) was stirred at 120° C. for 3 hours. After being concentrated in vacuo, the residue was purified by flash column chromatography on SiO$_2$ (Hex:EtOAc=9:1) to give Methyl 2-(2-ethoxy-2-oxoethyl)-4,4-dimethylcyclopent-1-enecarboxylate (2.23 g, 32%) as a yellow oil. $^1$H NMR (CDCl$_3$, Varian 400 MHz): δ 1.10 (3H, s), 1.17 (3H, s), 2.38-2.52 (4H, m), 3.69-3.71 (8H, m).

Step D: Methyl 3-(2-fluoro-4-iodophenylamino)-2,6,6-trimethyl-1-oxo-2,5,6,7-tetrahydro-1H-cyclopenta[c]pyridine-4-carboxylate

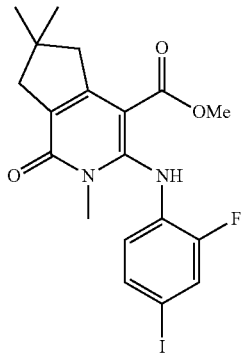 [SMILES: COC(=O)c1c2c(c(=O)n(C)c1Nc1ccc(I)cc1F)CC(C)(C)C2]

To a solution of diisopropylamine (1.83 mL, 12.8 mmol) in dry THF (10 mL) was added n-BuLi (5.12 mL, 12.8 mmol, 2.5 M solution in hexane) at −30° C. under Ar atmosphere. The mixture was stirred at −30° C. for 30 minutes and cooled to −78° C. After addition of a solution of methyl 2-(2-ethoxy-2-oxoethyl)-4,4-dimethylcyclopent-1-enecarboxylate (2.23 g, 9.86 mmol) in dry THF (29 mL) at −78° C., the reaction mixture was stirred at −78° C. for an additional 1 hour. After addition of 2-fluoro-4-iodo-N-((methylimino)methylene)aniline (intermediate 1, 4.08 g, 14.8 mmol) in THF (10 mL) at −78° C., the reaction mixture was stirred at −78° C. for 1 hour, and then quenched with aq. NH$_4$Cl. The mixture was extracted with EtOAc, and the combined organic layers were washed with brine, dried over Na$_2$SO$_4$, filtered and concentrated in vacuo. The residue was purified by flash column chromatography on SiO$_2$ (Hex:EtOAc=9:1 to 4:1) to give ethyl 3-(2-fluoro-4-iodophenylamino)-2,6,6-trimethyl-1-oxo-2,5,6,7-tetrahydro-1H-cyclopenta[c]pyridine-4-carboxylate (1.16 mg, 25%) as a yellow oil. $^1$H NMR (CDCl$_3$, Varian 400 MHz): δ 1.17 (6H, s), 2.65 (2H, brs), 2.97 (2H, brs), 3.31 (3H, s), 3.82 (3H, s), 6.37-6.41 (1H, m), 7.32-7.35 (1H, m), 7.47 (1H, dd, J=10.0, 2.0 Hz), 9.73 (1H, brs).

Step F: N-(2-(tert-butyldimethylsilyloxy)ethoxy)-3-(2-fluoro-4-iodophenylamino)-2,6,6-trimethyl-1-oxo-2,5,6,7-tetrahydro-1H-cyclopenta[c]pyridine-4-carboxamide

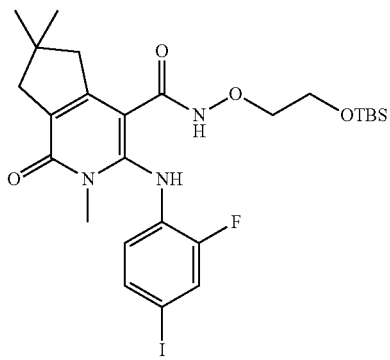 [SMILES: Cn1c(Nc2ccc(I)cc2F)c(C(=O)NOCCO[Si](C)(C)C(C)(C)C)c2c(c1=O)CC(C)(C)C2]

To a mixture of Ethyl 3-(2-fluoro-4-iodophenylamino)-2,6,6-trimethyl-1-oxo-2,5,6,7-tetrahydro-1H-cyclopenta[c]pyridine-4-carboxylate (100 mg, 0.213 mmol) and O-(2-(tert-butyldimethylsilyloxy)ethyl)hydroxylamine (intermediate 2, 425 mg, 0.425 mmol) in THF (1.0 mL) was added LiHMDS (1.0 M in THF/ethylbenzene, 1.06 mL, 1.06 mmol) at 0° C. After being stirred for 1 hour at room temperature, the mixture was quenched with saturated aq. NH$_4$Cl, extracted with EtOAc. The separated organic layer was washed water and brine, dried over Na$_2$SO$_4$, filtered and concentrated in vacuo. The residue was purified by column chromatography on SiO$_2$ (Hex:EtOAc=3:2 to 1:1) to give N-(2-(tert-butyldimethylsilyloxy)ethoxy)-3-(2-fluoro-4-iodophenylamino)-2,6,6-trimethyl-1-oxo-2,5,6,7-tetrahydro-1H-cyclopenta[c]pyridine-4-carboxamide (72.0 mg, 54%) as a yellow oil. $^1$H-NMR (CDCl$_3$, Varian, 400 MHz): δ 0.01 (6H, s), 0.87 (9H, s), 1.18 (6H, s), 2.67 (2H, brs), 2.81 (2H, brs), 3.34 (3H, s), 3.85-3.87 (2H, m), 3.97-3.99 (2H, m), 6.29 (1H, t, J=8.4 Hz), 7.29-7.31 (1H, m), 7.43 (1H, dd, J=10.0, 2.0 Hz), 8.72 (1H, brs).

Step G: 3-(2-fluoro-4-iodophenylamino)-N-(2-hydroxyethoxy)-2,6,6-trimethyl-1-oxo-2,5,6,7-tetrahydro-1H-cyclopenta[c]pyridine-4-carboxamide

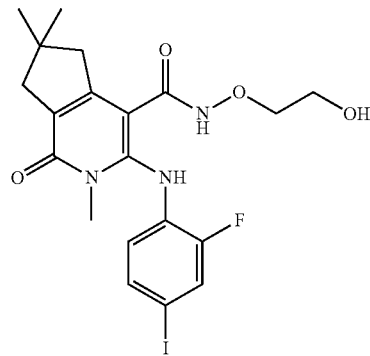 [SMILES: Cn1c(Nc2ccc(I)cc2F)c(C(=O)NOCCO)c2c(c1=O)CC(C)(C)C2]

To a solution of N-(2-(tert-butyldimethylsilyloxy)ethoxy)-3-(2-fluoro-4-iodophenylamino)-2,6,6-trimethyl-1-oxo-2,5,6,7-tetrahydro-1H-cyclopenta[c]pyridine-4-carboxamide (72.0 mg, 0.115 mmol) in THF (1.2 mL) was added TBAF (1.0 M in THF, 1.15 mL, 1.15 mmol) at room temperature. After being stirred for 1 hours at room temperature, the mixture was partitioned between EtOAc and water. The separated organic layer was washed with water and brine, dried over anhydrous Na$_2$SO$_4$, filtered and concentrated in vacuo. The residue was purified by column chromatography on SiO$_2$ (Hex:EtOAc=1:4 to 1:9) to give 3-(2-fluoro-4-iodophenylamino)-N-(2-hydroxyethoxy)-2,6,6-trimethyl-1-oxo-x2,5,6,7-tetrahydro-1H-cyclopenta[c]pyridine-4-carboxamide (17.6 mg, 30%) as a yellow oil. MS m/z=504.0 [M+1]$^+$ detected; $^1$H-NMR (CDCl$_3$, Varian, 400 MHz): δ 1.14 (6H, s), 2.62 (2H, brs), 2.77 (2H, brs), 3.34 (3H, s), 3.61-3.63 (2H, m), 3.87-3.89 (2H, m), 6.27 (1H, t, J=8.4 Hz), 7.26-7.29 (1H, m), 7.40 (1H, dd, J=10.0, 2.0 Hz).

Example 11

3-(2-chloro-4-iodophenylamino)-N-(2-hydroxyethoxy)-2-methyl-1-oxo-2,5,6,7-tetra hydro-1H-cyclopenta[c]pyridine-4-carboxamide

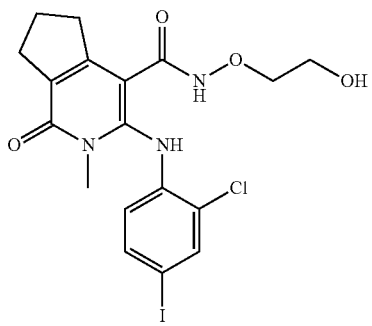

Step A: 1-(2-chloro-4-iodophenyl)-3-methylurea

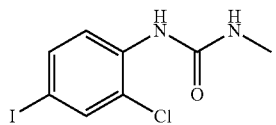

To a mixture of N,N'-carbonyldiimidazole (9.60 g, 59.2 mmol) and TEA (8.25 mL, 59.2 mmol) in dry DMF (40 mL) was slowly added 2-chloro-4-iodoaniline (10.0 g, 39.5 mmol) in dry DMF (20 mL) at 0° C. under a $N_2$ atmosphere. The reaction mixture was stirred overnight at room temperature. A solution of methylamine (4.83 mL, 47.3 mmol, 9.8 M solution in MeOH) was added thereto at 0° C. After stirring for 1 hour at room temperature, the reaction mixture was added to water/toluene (v/v=2/1) while stirring. The resulting solid was collected by filtration, rinsed with water and dried in vacuo to give 1-(2-chloro-4-iodophenyl)-3-methylurea (9.96 g, 81%) as a white solid, which was used for the next reaction without further purification. $^1$H NMR (DMSO-$d_6$, Varian 400 MHz): δ 2.65 (3H, d, J=4.4 Hz), 7.56 (1H, dd, J=8.8, 2.0 Hz), 7.73 (1H, d, J=2.0 Hz), 7.55 (1H, d, J=8.8 Hz), 8.07 (1H, brs).

Step B: 2-chloro-4-iodo-N-((methylimino)methylene)aniline

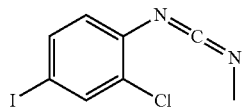

To a mixture of 1-(2-chloro-4-iodophenyl)-3-methylurea (9.96 g, 32.1 mmol), PPh$_3$ (16.8 g, 64.2 mmol) and TEA (17.9 mL, 128 mmol) in DCM (120 mL) was added CBr$_4$ (21.3 g, 64.2 mmol) at room temperature. The mixture was stirred at room temperature for 4 h. The mixture solvent was concentrated under reduce pressure. The residue purified by flash column chromatography on SiO$_2$ (Hex:E- tOAc=95:5) to give 2-chloro-4-iodo-N-((methylimino)methylene)aniline (9.38 g, quant.) as a red oil. $^1$H NMR (CDCl$_3$, Varian 400 MHz): δ 3.18 (3H, s), 7.03 (1H, d, J=8.4 Hz), 7.60-7.62 (1H, m), 7.81-7.82 (1H, m).

Step C: Ethyl 2-(2-ethoxy-2-oxoethyl)cyclopent-1-enecarboxylate

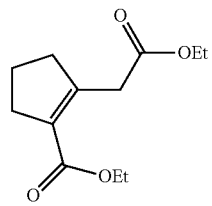 [SMILES: CCOC(=O)CC1=C(C(=O)OCC)CCC1]

A mixture of ethyl 2-oxocyclopentanecarboxylate (3.00 g, 19.2 mmol) and tributyl(2-ethoxy-2-oxoethyl)phosphonium bromide (10.6 g, 28.8 mmol) in toluene (3.0 mL) was stirred at 120° C. overnight. After being concentrated in vacuo, the residue was purified by flash column chromatography on SiO$_2$ (Hex:EtOAc=9:1) to give ethyl 2-(2-ethoxy-2-oxoethyl)cyclopent-1-enecarboxylate (1.94 g, 45%) as a yellow oil. $^1$H NMR (CDCl$_3$, Varian 400 MHz) δ 1.23-1.30 (6H, m), 1.84-1.91 (2H, m), 2.56-2.61 (2H, m), 2.65-2.68 (2H, m), 3.68 (2H, s), 4.12-4.21 (4H, m).

Step D: Ethyl 3-(2-chlor-4-iodophenylamino)-2-methyl-1-oxo-2,5,6,7-tetrahydro-1H-cyclopenta[c]pyridine-4-carboxylate

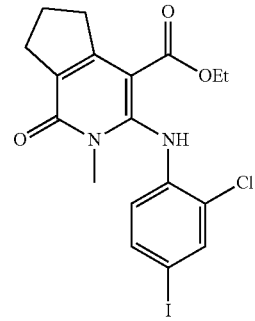 [SMILES: CCOC(=O)c1c2c(c(=O)n(C)c1Nc1ccc(I)cc1Cl)CCC2]

To a solution of ethyl 2-(2-ethoxy-2-oxoethyl)cyclopent-1-enecarboxylate (1.00 g, 4.42 mmol) in dry THF (17 mL) was added NaH (55%, 212 mg, 4.86 mmol) at 0° C. After being stirred at 0° C. for 30 minutes, a solution of 2-chloro-4-iodo-N-((methylimino)methylene)aniline (1.94 g, 6.63 mmol) in THF (5 mL) was added thereto at 0° C. After being stirred at room temperature for 1 hour, the reaction mixture was quenched with saturated aq. NH$_4$Cl and extracted with EtOAc. The residue was purified by flash column chromatography on SiO$_2$ (Hex:EtOAc=4:1) to give ethyl 3-(2-chloro-4-iodophenylamino)-2-methyl-1-oxo-2,5,6,7-tetrahydro-1H-cyclopenta[c]pyridine-4-carboxylate (233 mg, 11%) as a yellow oil.

$^1$H NMR (CDCl$_3$, Varian 400 MHz) δ 1.35 (3H, t, J=7.2 Hz), 2.05 (2H, t, J=7.6 Hz), 2.84 (2H, t, J=7.6 Hz), 3.20-3.28 (5H, m), 4.29 (2H, q, J=7.2 Hz), 6.28 (1H, d, J=8.4 Hz), 7.42 (1H, dd, J=8.4, 2.0 Hz), 7.75 (1H, d, J=1.6 Hz), 9.71 (1H, brs).

Step E: N-(2-(tert-butyldimethylsilyloxy)ethoxy)-3-(2-chloro-4-iodophenylamino)-2-methyl-1-oxo-2,5,6,7-tetrahydro-1H-cyclopenta[c]pyridine-4-carboxamide

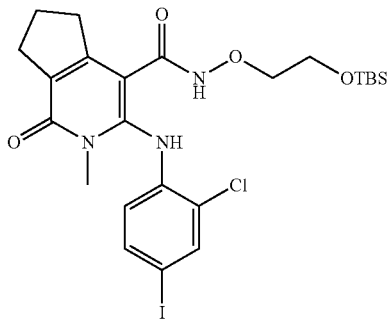 [SMILES: Cn1c(Nc2ccc(I)cc2Cl)c(C(=O)NOCCO[Si](C)(C)C(C)(C)C)c2c(c1=O)CCC2]

To a mixture of ethyl 3-(2-chloro-4-iodophenylamino)-2-methyl-1-oxo-2,5,6,7-tetrahydro-1H-cyclopenta[c]pyridine-4-carboxylate (230 mg, 0.487 mmol) and O-(2-(tert-butyldimethylsilyloxy)ethyl)hydroxylamine (intermediate 2, 186 mg, 0.973 mmol) in THF (2.4 mL) was added LiHMDS (1.0 M in THF/ethylbenzene, 2.43 mL, 2.43 mmol) at 0° C. After being stirred for 1 hour at room temperature, the mixture was quenched with saturated aq. NH$_4$Cl, extracted with EtOAc. The separated organic layer was washed water and brine, dried over Na$_2$SO$_4$, filtered and concentrated in vacuo. The residue was purified by column chromatography on SiO$_2$ (Hex:EtOAc=1:1) to give N-(2-(tert-butyldimethylsilyloxy)ethoxy)-3-(2-chloro-4-iodophenylamino)-2-methyl-1-oxo-2,5,6,7-tetrahydro-1H-cyclopenta[c]pyridine-4-carboxamide (108 mg, 36%) as a yellow oil. $^1$H-NMR (CDCl$_3$, Varian, 400 MHz): δ 0.06 (6H, s), 0.86 (9H, s), 2.10 (2H, t, J=7.6 Hz), 2.86 (2H, t, J=7.2 Hz), 3.02 (2H, t, J=7.2 Hz), 3.33 (3H, s), 3.85-3.87 (2H, m), 3.96-3.99 (2H, m), 6.18 (1H, d, J=8.4 Hz), 7.38 (1H, dd, J=8.4, 2.0 Hz), 7.71 (1H, d, J=2.0 Hz), 8.74 (1H, brs), 8.84 (1H, brs).

Step F: 3-(2-chloro-4-iodophenylamino)-N-(2-hydroxyethoxy)-2-methyl-1-oxo-2,5,6,7-tetrahydro-1H-cyclopenta[c]pyridine-4-carboxamide

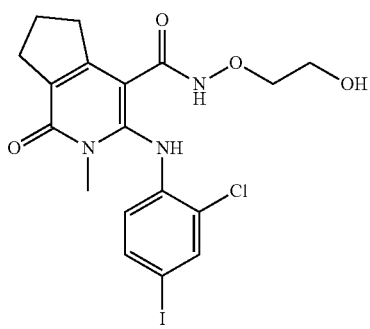

To a solution of N-(2-(tert-butyldimethylsilyloxy)ethoxy)-3-(2-chloro-4-iodophenylamino)-2-methyl-1-oxo-2,5,6,7-tetrahydro-1H-cyclopenta[c]pyridine-4-carboxamide (100 mg, 0.162 mmol) in THF (1.6 mL) was added TBAF (1.0 M in THF, 1.62 mL, 1.62 mmol) at room temperature. After being stirred for 1 hour at room temperature, the mixture was partitioned between EtOAc and water. The separated organic layer was washed with water and brine, dried over anhydrous Na$_2$SO$_4$, filtered and concentrated in vacuo. The residue was purified by column chromatography on SiO$_2$ (EtOAc: MeOH=95:5) to give 3-(2-chloro-4-iodophenylamino)-N-(2-hydroxyethoxy)-2-methyl-1-oxo-2,5,6,7-tetrahydro-1H-cyclopenta[c]pyridine-4-carboxamide (27.0 mg, 33%) as a yellow solid. MS m/z=504.0 [M+1]$^+$ detected; $^1$H-NMR (DMSO-d$_6$, Varian, 400 MHz): δ 1.96-2.03 (2H, m), 2.69 (2H, t, J=7.2 Hz), 286 (2H, t, J=7.2 Hz), 3.26 (3H, s), 3.44 (2H, brs), 3.62-3.65 (2H, m), 4.65 (1H, brs), 6.28 (1H, d, J=8.4 Hz), 7.44 (1H, dd, J=8.4, 2.0 Hz), 7.72 (1H, d, J=2.0 Hz), 8.00 (1H, brs), 11.09 (1H, brs).

Biological Activity

MEK Kinase Assay

Materials and Preparation of Reagents:

The LANCE Ultra assay kit was purchased from PerkinElmer. The ULight™-MBP peptide, Europium labeled Antibody and LANCE Detection buffer were purchased from PerkinElmer. The APT and dimethylsulfoxide were purchased from Sigma-Aldrich. The 5× Kinase buffer were purchased from Invitrogen. The MAP kinase 1 (Mek1), inactive Erk1 were purchased from Millipore.

Assay Protocol and Data Analysis:

A Mek1 kinase assay (LANCE, PerkinElmer) was developed for supporting compound profiling and lead optimization. In this assay, un-phosphorylated/inactive Erk1 (Millipore) was used as the substrate for Mek1 (Millipore). Then the phosphorylated Erk1 was able to phosphorylate ULight™-MBP peptide (PerkinElmer). The phosphorylated peptide was detected by Europium-anti-phospho-MBP (PerkinElmer). In a reaction, the activity of Mek1 (0.5 nM) was measured in a buffer containing 50 μM ATP, 2 nM inactive Erk1, 2 nM ULight™-MBP peptide, and a compound for 90 min at 23° C. After quenching the reaction with xxx, 2 nM Europium-anti-phospho-MBP was added to the reaction mixture and incubated for 60 min, followed by a detection using EnVision Multilabel Plate Reader (PerkinElmer). The IC$_{50}$ values were derived through a curve fitting using GraphPad Prism5.

Cell Viability Assay

Materials and Preparation of Reagents:

The CellTiter-Glo® assay was purchased from Promega. All the reagents and plates for cell culture were purchased Invitrogen Life Technology and Nunc, respectively.

Generation of Cell Based IC$_{50}$ Data

To investigate whether a compound is able to inhibit the activity of MEK in cells, a mechanism-based assay using COLO205 cell line (Colon cancer) and M14 cell line (Melanoma) were developed. COLO205 cells and M14 cells were cultured in a tissue culture flask to 80% confluence in RPMI1640 plus 10% fetal bovine serum. Cells were collected and plated onto 96 well culture plates at 2×10$^2$ cells/well. Plates were incubated overnight at 37° C. in a 5% CO$_2$ incubator to allow cells to adhere. Various concentrations of MEK inhibitors were added to the plates and incubated at 37° C. for 72 hours. After 72 hours, 20 μl of CellTiter-Glo® reagent was added to each well. Mix by orbital shaking for 2 min, then incubates at room temperature for 15 min. Cell lysate were transferred into a 96 well white plate (Thermo). Plates were read out by EnVision Multilabel Plate Reader. The data were analyzed using GraphPad Prism5.

Biological Data for Select Compounds

Select compounds prepared as described above were assayed according to the biological procedures described herein. The results are given in the table below:

| Structure | IC$_{50}$ (nM) | | |
|---|---|---|---|
| | Enzymatic assay | Cell-based assay (COLO205) | Cell-based assay (M14) |
| (structure) | <1000 | <500 | <500 |
| (structure) | <10000 | <50000 | <50000 |
| (structure) | <500 | <5 | <10 |
| (structure) | <5000 | <50 | <500 |
| (structure) | <500 | <5 | <50 |

-continued
| Structure | IC$_{50}$ (nM) | | |
|---|---|---|---|
| | Enzymatic assay | Cell-based assay (COLO205) | Cell-based assay (M14) |
| 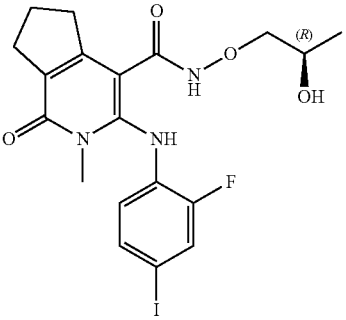 | <1000 | <10 | <100 |
| 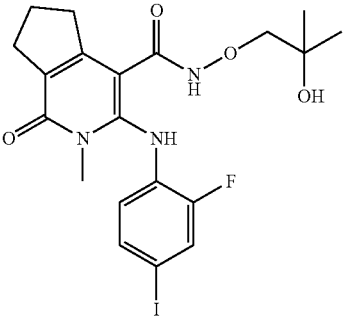 [SMILES: Cn1c(Nc2ccc(I)cc2F)c(C(=O)NOCC(C)(C)O)c2c(c1=O)CCC2] | <5000 | <5 | <500 |
| 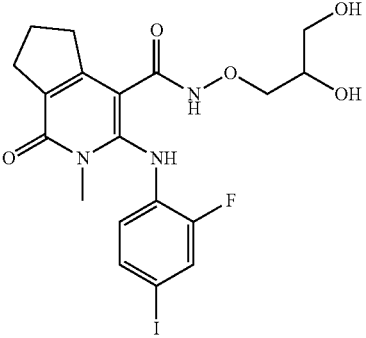 [SMILES: Cn1c(Nc2ccc(I)cc2F)c(C(=O)NOCC(O)CO)c2c(c1=O)CCC2] | <500 | <5 | <50 |
| 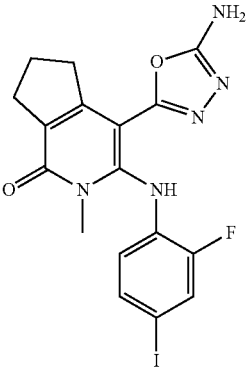 [SMILES: Cn1c(Nc2ccc(I)cc2F)c(-c2nnc(N)o2)c2c(c1=O)CCC2] | <5000 | <50 | <1000 |

| Structure | IC$_{50}$ (nM) | | |
|---|---|---|---|
| | Enzymatic assay | Cell-based assay (COLO205) | Cell-based assay (M14) |
| (structure) | <500 | <50 | <100 |
| (structure) | <500 | <5 | <50 |

Toxicity Data

CZ 3113 Toxicity Study by Oral Administration for 28 Days

To evaluate the potential toxicity, test article, CZ3113, was administered orally for 28 days to Sprague-Dawley rats.

Male and female Sprague-Dawley rats, 6 weeks of age at onset of the study, were assigned to 6 experimental groups as follow: (1) rats control group (2 animals/sex/group) (2) rats that received 1 mg/kg/day (lowest dose; 2 animals/sex/group) (3) rats that received 2.5 mg/kg/day (low dose; 2 animals/sex/group) (4) rats that received 5 mg/kg/day (mid-low dose; 2 animals/sex/group) (5) rats that received 10 mg/kg/day (mid dose; 2 animals/sex/group) (6) rats that received 25 mg/kg/day (high dose; 2 animals/sex/group). Each article was in vehicle (Captisol). Body weight was measured on a daily basis to determine toxicity.

Figure 2:
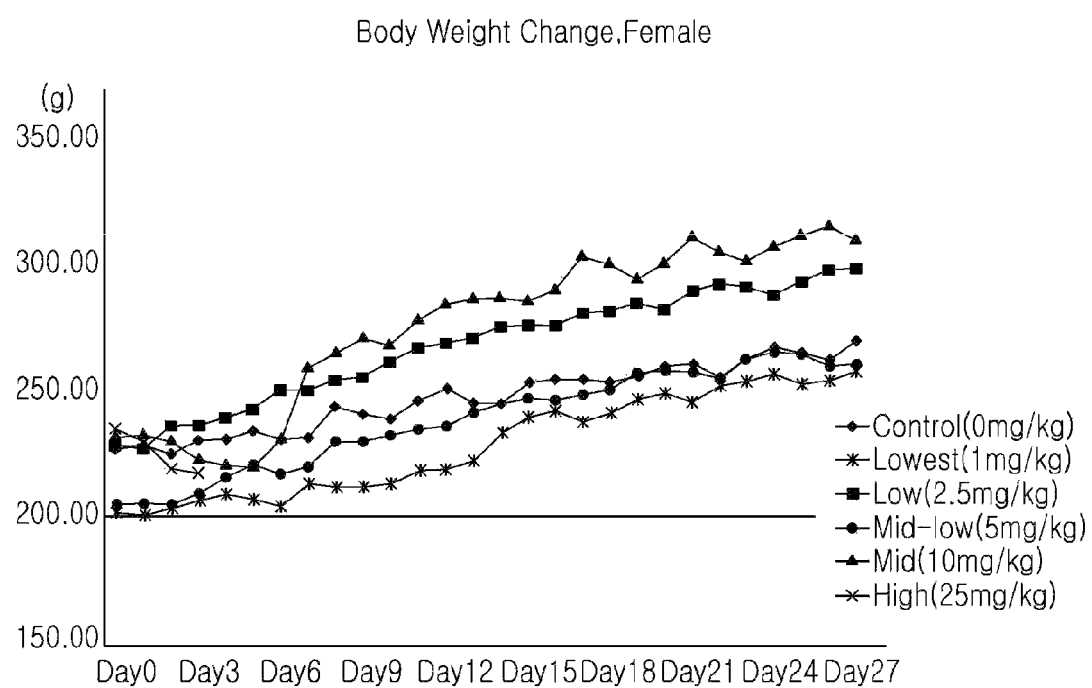
FIG. 2 shows the change in body weight in the female (data of CZ3113).
Figure 3:
FIG. 3 shows the change in body weight (data of Example 3).

As shown in FIG. 1, in the male, high dose group died at the third day. Mid-low group (5 mg/kg) showed decrease of body weight after 24 days. Mid group showed decrease of body weight after 14 days. Body weights of control, lowest, low groups were gradually increased. As shown in FIG. 2, in the female, high dose group died at the third day. Body weights of control, lowest, low, mid-low, mid groups were gradually increased.

Example 3

Toxicity Study by Oral Administration for 8 Days

To evaluate the potential toxicity, test article, Example 3, was administered orally for 8 days to Sprague-Dawley rats.

Male and female Sprague-Dawley rats, 6 weeks of age at onset of the study, were assigned to 2 experimental groups as follow: (1) 2 male rats treated 5, 5, 10, 20, 40, 80, 160, 320 mg/kg each day with doses escalating for 8 days (2) 2 female rats treated 5, 5, 10, 20, 40, 80, 160, 320 mg/kg each day with doses escalating for 8 days. Each article was in vehicle (Captisol).

Body weight was measured on a daily basis to determine toxicity. All groups were sacrificed at 9th day.

As a result, all animals survived until their scheduled sacrifice. No mortality was observed. Body weights of male groups decreased at day 6 and day 8. Body weights of female groups decreased after 6 days.

The invention claimed is:

1. A compound of formula II

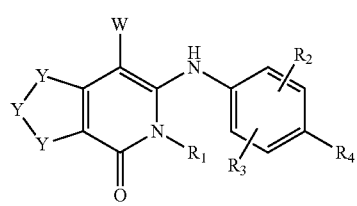

Formula II wherein

R$_1$ is H, C$_1$-C$_6$ alkyl, C$_3$-C$_6$ cycloalkyl, C$_2$-C$_6$ alkenyl, C$_5$-C$_6$ cycloalkenyl or C$_2$-C$_6$ alkynyl; wherein each alkyl, cycloalkyl, alkenyl, cycloalkenyl or alkynyl group is optionally substituted with 1-3 substituents selected independently from the group consisting of halogen, hydroxy, C$_1$-C$_4$ alkyl, C$_1$-C$_4$ alkoxy, cyano, cyanomethyl, trifluoromethyl, difluoromethoxy and phenyl, and one or two ring carbon atoms of said $C_3$-$C_6$ cycloalkyl groups are optionally replaced with, independently, O, N, or S; and $R_2$, $R_3$, and $R_4$ are independently selected from hydrogen, halogen, cyano, nitro, trifluoromethyl, difluoromethyl, fluoromethyl, fluoromethoxy, difluoromethoxy, trifluoromethoxy, azido, —$SR_9$, —$OR_9$, —$C(O)R_9$, —$NR_{10}C(O)OR_{12}$, —$OC(O)R_9$, —$NR_{10}$, —$S(O)_jR_{12}$, —$S(O)_jNR_9R_{10}$, —$S(O)_jNR_{10}C(O)R_9$, —$C(O)NR_{10}S(O)_jR_{12}$, —$S(O)_jR_{12}$, —$NR_{10}C(O)R_9$, —$C(O)NR_9R_{10}$, —$NR_{11}C(O)NR_9R_{10}$, —$NR_{11}C(NCN)NR_9R_{10}$, —$NR_9R_{10}$ and $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR_{10}R_{11})_m$-aryl, aryl, arylalkyl, heteroaryl, heteroarylalkyl, heterocyclyl, heterocyclylalkyl, —$O(CR_{10}R_{10})_m$-aryl, —$NR_{10}(CR_{10}R_{11})_m$-aryl, —$O(CR_{10}R_{11})_m$-heteroaryl, —$NR_{10}(CR_{10}R_{11})_m$-heteroaryl, —$O(CR_{10}R_{11})_m$-heterocyclyl, —$NR_{10}(CR_{10}R_{11})_m$-heterocyclyl, and —$S(C_1$-$C_2$ alkyl) optionally substituted with fluorine atoms;

$R_9$ is selected from the group consisting of hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is unsubstituted or substituted with 1-3 substituents independently selected from the group consisting of halogen, $C_1$-$C_4$ alkyl, hydroxyl and amino;

$R_{10}$ is selected from hydrogen or $C_1$-$C_6$ alkyl where alkyl may be unsubstituted or substituted with 1-3 substituents independently selected from the group consisting of halogen, $C_1$-$C_4$ alkyl, hydroxyl and amino; or $R_9$ and $R_{10}$ can be taken together with the atom to which they are attached to form a 4 to 10 membered heteroaryl or heterocyclic ring, each of which is unsubstituted or substituted with 1-3 substituents independently selected from the group consisting of halogen, $C_1$-$C_4$ alkyl, hydroxyl and amino;

$R_{11}$ is selected from hydrogen or $C_1$-$C_6$ alkyl where alkyl may be unsubstituted or substituted with 1-3 substituents independently selected from the group consisting of halogen, $C_1$-$C_4$ alkyl, hydroxyl and amino; or $R_{10}$ and $R_{11}$ can be taken together with the atom to which they are attached to form a 4 to 10 membered carbocyclic, heteroaryl or heterocyclic ring, each of which is unsubstituted or substituted with 1-3 substituents independently selected from the group consisting of halogen, $C_1$-$C_4$ alkyl, hydroxyl and amino, and $R_{12}$ is selected from trifluoromethyl, $C_1$-$C_{10}$ alkyl, $C_3$-$C_{10}$ cycloalkyl, aryl, arylalkyl, heteroaryl, heteroarylalkyl, heterocyclyl, and heterocyclylalkyl, where each alkyl, cycloalkyl, aryl, heteroaryl and heterocyclyl unsubstituted or substituted with 1-3 substituents independently selected from the group consisting of halogen, $C_1$-$C_4$ alkyl, hydroxyl and amino;

W is —$C(O)OR_6$, —$C(O)NR_6R_7$, —$C(O)NR_7OR_6$, —$C(O)R_7OR_6$, heteroaryl, heterocyclyl, —$NHSO_2R_6$, —$NHC(O)OR_6$, —$NHC(O)NR_6R_7$, —$NHC(O)R_6$, —$NR_6R_7$, —$C(O)(C_3$-$C_{10}$ cycloalkyl), —$C(O)(C_1$-$C_{10}$ alkyl), —$C(O)(aryl)$, —$C(O)(heteroaryl)$, —$C(O)(heterocyclyl)$, —$C(O)NHSO_2CH_3$, or —$CR_6OR_6$, wherein any of said heteroaryl, heterocyclyl, —$C(O)OR_6$, —$C(O)NR_6R_7$, —$C(O)NR_7OR_6$, —$C(O)R_7OR_6$, —$NHSO_2R_6$, —$NHC(O)OR_6$, —$NHC(O)NR_6R_7$, —$NHC(O)R_6$, —$NR_6R_7$, —$C(O)(C_3$-$C_{10}$ cycloalkyl), —$C(O)(C_1$-$C_{10}$ alkyl), —$C(O)(aryl)$, —$C(O)(heteroaryl)$, —$C(O)(heterocyclyl)$, —$C(O)NHSO_2CH_3$ and —$CR_6OR_6$ are optionally substituted independently with one or more groups independently selected from halogen, cyano, nitro, azide, —$NR_6R_7$, —$OR_6$, $C_1$-$C_{10}$ alkyl, $C_2$-$C_{10}$ alkenyl, and $C_2$-$C_{10}$ alkynyl, cycloalkyl and heterocycloalkyl, wherein any of said $C_1$-$C_{10}$ alkyl, $C_2$-$C_{10}$ alkenyl, $C_2$-$C_{10}$ alkynyl, cycloalkyl and heterocycloalkyl are optionally substituted independently with 1 or more groups independently selected from —$NR_6R_7$ and —$OR_6$;

$R_6$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that is not substituted on a aryl or heteroaryl), halogen, cyano, nitro, trifluoromethyl, difluoromethoxy, trifluoromethoxy, azido, —$NR_{13}SO_2R_{16}$, —$SO_2NR_{13}R_{14}$, —$C(O)R_{13}$, —$C(O)OR_{13}$, —$OC(O)R_{13}$, —$NR_{13}C(O)OR_{16}$, —$NR_{13}C(O)R_{14}$, —$C(O)NR_{13}R_{14}$, —$SR_{13}$, —$S(O)R_{16}$, —$SO_2R_{16}$, —$NR_{13}R_{14}$, —$NR_{13}C(O)NR_{14}R_{15}$, —$NR_{13}C(NCN)NR_{14}R_{15}$, —$OR_{13}$, aryl, heteroaryl, arylalkyl, heteroarylalkyl, heterocyclyl, and heterocyclylalkyl, or $R_6$ and $R_7$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —$NR_{13}SO_2R_{16}$, —$SO_2NR_{13}R_{14}$, —$C(O)R_{13}$, —$C(O)OR_{13}$, —$OC(O)R_{13}$, —$NR_{13}C(O)OR_{16}$, —$NR_{13}C(O)R_{14}$, —$C(O)NR_{13}R_{14}$, —$SO_2R_{16}$, —$NR_{13}R_{14}$, —$NR_{13}C(O)NR_{14}R_{15}$, —$NR_{13}C(NCN)NR_{14}R_{15}$, —$OR_{13}$, aryl, heteroaryl, arylalkyl, heteroarylalkyl, heterocyclyl, and heterocyclylalkyl;

$R_7$ is hydrogen or $C_1$-$C_6$ alkyl;

each Y is independently $CH_2$, $C(CH_3)_2$ or $CR_{17}R_{17}$;

m is 0, 1, 2, 3, 4 or 5; and j is 1 or 2;

$R_5$ is H, F, Cl, Br, $CF_3$, CN, —$C(O)R_6$, —$C(O)OR_6$, —$C(O)NR_6R_7$, —$NR_6R_7$, —$NR_6C(O)R_7$, —$NR_8C(O)OR_7$, —$NR_8C(O)NR_6R_7$, —$NR_8$, —$SO_2NR_6R_7$, —$OC(O)R_6$, —$OC(O)OR_6$, —$OC(O)NR_6R_7$, —$SR_6$, —$SO_2R_6$, —$SO_2NR_6R_7$, $C_1$-$C_{12}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, or heterocyclylalkyl;

$R_8$ is selected from the group consisting of trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heteroarycycloalkyl, heterocyclyl, and heterocyclylalkyl, where each alkyl, alkenyl, alkynyl, cycloalkyl, cycloalkylalkyl, aryl, arylalkyl, heteroaryl, heteroarylalkyl, heterocyclylalkyl, heteroarycycloalkyl, and heterocyclyl is unsubstituted or substituted with 1-3 substituents selected independently from halogen, hydroxyl, $C_1$-$C_4$ alkyl, $C_1$-$C_4$ alkoxy, cyano, trifluoromethyl, difluoromethoxy, phenyl or substituted phenyl with 1-3 substituents selected independently from halogen, hydroxyl, $C_1$-$C_4$ alkyl, $C_1$-$C_4$ alkoxy, cyano trifluoromethyl, or difluoromethoxy;

R$_{13}$, R$_{14}$ and R$_{15}$ independently are hydrogen, lower alkyl, lower alkenyl, aryl and arylalkyl, and R$_{16}$ is lower alkyl, lower alkenyl, aryl and arylalkyl, or any two of R$_{13}$, R$_{14}$, R$_{15}$ or R$_{16}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

each R$_{17}$ is independently selected from the group consisting of hydrogen, halo, nitro, cyano, thio, oxy, hydroxy, carbonyloxy, C$_1$-C$_{10}$ alkoxy, C$_4$-C$_{12}$ aryloxy, heteroC$_1$-C$_{10}$ aryloxy, carbonyl, oxycarbonyl, aminocarbonyl, amino, C$_1$-C$_{10}$ alkylamino, sulfonamido, imino, sulfonyl, sulfinyl, C$_1$-C$_{10}$ alkyl, haloC$_1$-C$_{10}$ alkyl, hydroxylC$_1$-C$_{10}$ alkyl, carbonylC$_1$-C$_{10}$ alkyl, thiocarbonylC$_1$-C$_{10}$ alkyl, sulfonylC$_1$-C$_{10}$ alkyl, sulfinylC$_1$-C$_{10}$ alkyl, C$_1$-C$_{10}$ alzalkyl, iminoC$_1$-C$_{10}$ alkyl, C$_3$-C$_{12}$ cycloalkylC$_1$-C$_5$ alkyl, heteroC$_3$-C$_{12}$ cycloalkylC$_1$-C$_{10}$ alkyl, arylC$_1$-C$_{10}$ alkyl, heteroC$_1$-C$_{10}$ arylC$_1$-C$_5$ alkyl, C$_9$-C$_{12}$ bicycloarylC$_1$-C$_5$ alkyl, heteroC$_8$-C$_{12}$ bicycloarylC$_1$-C$_5$ alkyl, C$_3$-C$_{12}$ cycloalkyl, heteroC$_3$-C$_{12}$ cycloalkyl, C$_9$-C$_{12}$ bicycloalkyl, heteroC$_3$-C$_{12}$ bicycloalkyl, C$_4$-C$_{12}$ aryl, heteroC$_1$-C$_{10}$ aryl, C$_9$-C$_{12}$ bicycloaryl and heteroC$_4$-C$_{12}$ bicycloaryl, each substituted or unsubstituted, or two R$_{17}$ are taken together to form a substituted or unsubstituted ring, or a pharmaceutically acceptable salt, solvate, polymorph, ester, tautomer or prodrug thereof.

2. A compound according to claim 1, wherein

R$_1$ is C$_1$-C$_6$ alkyl;

R$_2$, R$_3$, and R$_4$ are independently selected form H and halogen;

W is —C(O)NR$_6$R$_7$, —C(O)NR$_7$OR$_6$, —C(O)R$_7$OR$_6$, —NHSO$_2$R$_6$ or heteroaryl;

R$_6$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, or heterocyclylalkyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo (with the proviso that is not substituted on a aryl or heteroaryl), halogen, cyano, nitro, trifluoromethyl, difluoromethoxy, trifluoromethoxy, azido, —NR$_{13}$SO$_2$R$_{16}$, —SO$_2$NR$_{13}$R$_{14}$, —C(O)R$_{13}$, —C(O)OR$_{13}$, —OC(O)R$_{13}$, —NR$_{13}$C(O)OR$_{16}$, —NR$_{13}$C(O)R$_{14}$, —C(O)NR$_{13}$R$_{14}$, —SR$_{13}$, —S(O)R$_{16}$, —SO$_2$R$_{16}$, —NR$_{13}$R$_{14}$, —NR$_{13}$C(O)NR$_{14}$R$_{16}$, —NR$_{13}$C(NCN)NR$_{14}$R$_{15}$, —OR$_{13}$, aryl, heteroaryl, arylalkyl, heteroarylalkyl, heterocyclyl, and heterocyclylalkyl, or R$_6$ and R$_7$ together with the atom to which they are attached form a 4 to 10 membered carbocyclic, heteroaryl or heterocyclic ring, wherein any of said carbocyclic, heteroaryl or heterocyclic rings are optionally substituted with one or more groups independently selected from halogen, cyano, nitro, trifluoromethyl, difluoromethoxy, trifluoromethoxy, azido, —NR$_{13}$SO$_2$R$_{16}$, —SO$_2$NR$_{13}$R$_{14}$, —C(O)R$_{13}$, —C(O)OR$_{13}$, —OC(O)R$_{13}$, —NR$_{13}$C(O)OR$_{16}$, —NR$_{13}$C(O)R$_{14}$, —C(O)NR$_{13}$R$_{14}$, —SO$_2$R$_{16}$, —NR$_{13}$R$_{14}$, —NR$_{13}$C(O)NR$_{14}$R$_{15}$, —NR$_{13}$C(NCN)NR$_{14}$R$_{15}$, —OR$_{13}$, aryl, heteroaryl, arylalkyl, heteroarylalkyl, heterocyclyl, and heterocyclylalkyl;

R$_7$ is hydrogen or C$_1$-C$_6$ alkyl;

R$_{13}$, R$_{14}$ and R$_{15}$ independently are hydrogen, lower alkyl, lower alkenyl, aryl and arylalkyl, and R$_{16}$ is lower alkyl, lower alkenyl, aryl and arylalkyl, or any two of R$_{13}$, R$_{14}$, R$_{15}$ or R$_{16}$ together with the atom to which they are attached form a 4 to 10 membered carbocyclic, heteroaryl or heterocyclic ring, wherein any of said alkyl, alkenyl, aryl, arylalkyl carbocyclic rings, heteroaryl rings or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

each Y is independently CH$_2$ or C(CH$_3$)$_2$;

or a pharmaceutically acceptable salt, solvate, polymorph, ester, tautomer or prodrug thereof.

3. The compound according to claim 1, wherein structures are:

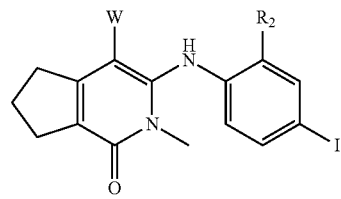

wherein

W and R$_2$ are defined as claim 1.

4. The compound of any of claim 3, wherein W is —C(O)NHR$_6$ and R$_6$ is selected from

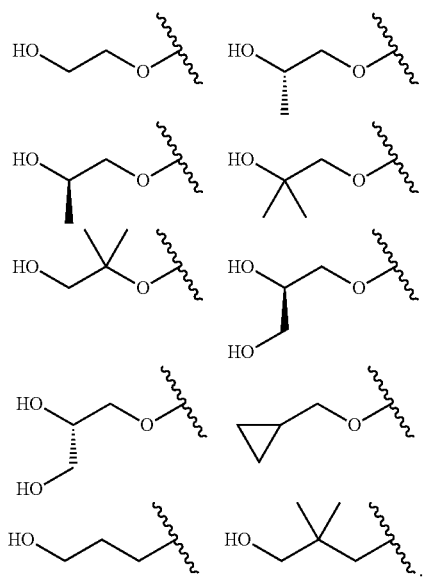

5. The compound of any of claim 3, wherein W is —NHSO$_2$R$_6$ and R$_6$ is selected from

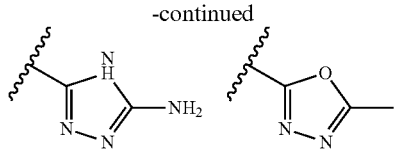
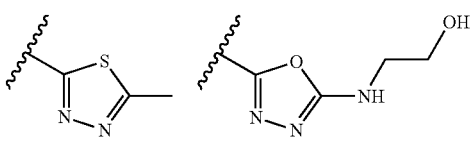
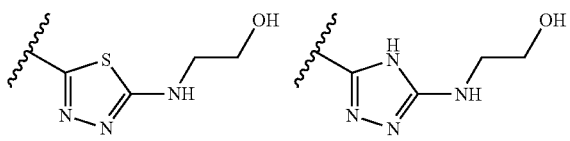
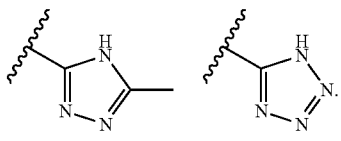
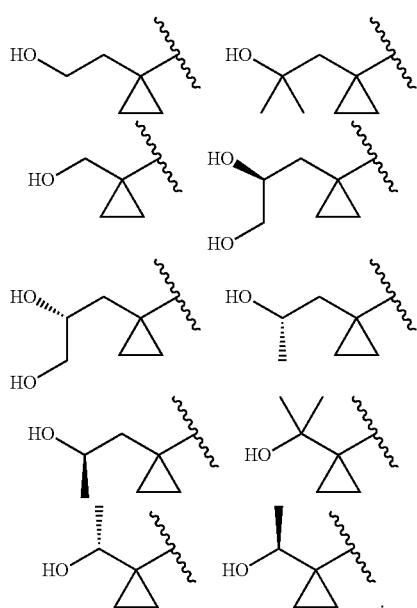
6. The compound of any of claim 3, wherein W is selected from the structures:
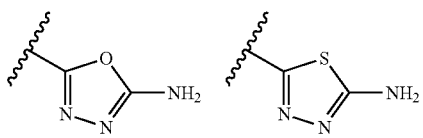
7. A pharmaceutical composition comprising a pharmaceutically effective amount of a compound of claim 1 or a pharmaceutically acceptable salt, solvate, polymorphpolymorph, ester, tautomer or prodrug thereof, and a pharmaceutically acceptable carrier.
* * * * *